United States Patent
Maltz

(10) Patent No.: US 12,004,895 B2
(45) Date of Patent: Jun. 11, 2024

(54) METRIC-BASED DATA MANAGEMENT FOR X-RAY IMAGING SYSTEMS

(71) Applicant: GE Precision Healthcare LLC, Milwaukee, WI (US)

(72) Inventor: Jonathan S. Maltz, Oakland, CA (US)

(73) Assignee: GE Precision Healthcare LLC, Waukesha, WI (US)

( * ) Notice: Subject to any disclaimer, the term of this patent is extended or adjusted under 35 U.S.C. 154(b) by 265 days.

(21) Appl. No.: 17/697,390

(22) Filed: Mar. 17, 2022

(65) Prior Publication Data
US 2023/0293135 A1    Sep. 21, 2023

(51) Int. Cl.
*A61B 6/00* (2006.01)
*A61B 6/03* (2006.01)
*A61B 6/42* (2024.01)

(52) U.S. Cl.
CPC .......... *A61B 6/56* (2013.01); *A61B 6/035* (2013.01); *A61B 6/4241* (2013.01)

(58) Field of Classification Search
CPC ......... A61B 6/56; A61B 6/035; A61B 6/4241; A61B 6/5217; A61B 6/032; G01T 1/17; G01T 1/2985
See application file for complete search history.

(56) References Cited

U.S. PATENT DOCUMENTS

| | | |
|---|---|---|
| 8,183,535 B2 | 5/2012 | Danielsson et al. |
| 11,166,683 B2 | 11/2021 | Carbonne Dit Leychert Garenne et al. |
| 2013/0003912 A1* | 1/2013 | De Man ............. A61B 6/032 378/5 |
| 2016/0232691 A1 | 8/2016 | Nishii |

FOREIGN PATENT DOCUMENTS

EP    0514968 A1    11/1992

OTHER PUBLICATIONS

Tapiovaara and Wagner, "SNR and DQE analysis of broad spectrum X-ray imaging", Phys. Med. Biol. 30, 519.
Alvarez, Macovski, "Energy-selective reconstructions in X-ray computerized tomography", Phys Med Biol. 1976; 21(5):733-744.
(Continued)

*Primary Examiner* — Kiho Kim

(57) ABSTRACT

An X-ray imaging system includes a gantry with moving and stationary parts on moving and stationary sides, respectively, the parts communicatively coupled via a data communication system. The moving part includes an X-ray source to emit X-rays; an X-ray detector configured to generate detector data; and on-moving-gantry processing circuitry. The on-moving-gantry processing circuitry is configured to determine, for each of a number of partial data sets of the generated detector data, a metric value of at least one metric, the metric value being translatable into a type of data management for the partial data set among at least two different types of data management. The processing circuitry further configured to decide, for each partial data set, how it set is to be treated based on the determined metric value of the at least one metric and to selectively effectuate data management according to the corresponding type of data management.

26 Claims, 17 Drawing Sheets

(56) References Cited

OTHER PUBLICATIONS

Roessl and Proksa, "K-edge imaging in X-ray computed tomography using multi-bin photon counting detectors", Phys. Med. Biol. 52 (2007), 4679-4696.
Glenn F. Knoll, "Radiation Detection and Measurement", 3rd edition, John Wiley & Sons Inc, pp. 632-642 (submission pending).
Grönberg F, Danielsson M, Sjölin M., "Count statistics of non-paralyzable photon-counting detectors with nonzero pulse length", Med Phys. 2018;45(8):3800-3811 (submission pending).
Sabbatucci L, Fernández JE., "First principles pulse pile-up balance equation and fast deterministic solution", Radiation Physics Chemistry, 2017;137:12-17 (submission pending).
Cammin J, Kappler S, Weidinger T, Taguchi K. "Evaluation of models of spectral distortions in photon-counting detectors", J Med Imaging. 2016;3(2) (submission pending).
Feng R, Rundle D, Wang G, "Neural-networks-based Photon-Counting Data Correction: Pulse Pileup Effect", In: IEEE.; 2018:1-14.
Alvarez, ArXiv, "Near optimal neural network estimator for spectral X-ray photon counting data with pileup", 2017:1-11.
International Application No. PCT/US2023/064453 filed Mar. 15, 2023—International Search Report and Written Opinion dated Sep. 8, 2023; 20 pages.

\* cited by examiner

METRIC-BASED DATA MANAGEMENT FOR X-RAY IMAGING SYSTEMS

TECHNICAL FIELD

The proposed technology relates to X-ray technology and X-ray imaging and corresponding data management and data processing tasks. In particular, the proposed technology relates to an X-ray imaging system such as a Computed Tomography (CT) system and a method of operating such an X-ray imaging system as well as a corresponding computer program and computer-program product, for improved data management.

BACKGROUND

Radiographic imaging such as Computed Tomography (CT) imaging systems have been used for years in medical applications, such as for medical diagnostics and treatment.

Normally, an X-ray imaging system such as a CT imaging system includes an X-ray source and an X-ray detector array consisting of multiple detectors comprising one or many detector elements, for independent measuring of X-ray intensities. The X-ray source emits X-rays, which pass through a subject or object to be imaged and are then received by the detector array. The X-ray source and detector array are typically arranged to rotate on a rotating member of a gantry, around the subject or object. The emitted X-rays are attenuated by the subject or object as they pass through, and the resulting transmitted X-rays are measured by the detector. The measured data may then be used to reconstruct images of the subject or object.

It may be useful with a brief overview of an illustrative general X-ray imaging system according to the prior art with reference to FIG. 1A. In this illustrative example the X-ray imaging system 1 comprises an X-ray source 10, an X-ray detector system 20 and an associated image processing system or device 30. In general, the X-ray detector system 20 is configured to register radiation from the X-ray source 10, which optionally has been focused by optional X-ray optics or collimators and passed through an object, a subject or a part thereof. The X-ray detector system 20 is connectable to the image processing system 30 via suitable analog read-out electronics, which is at least partly integrated in the X-ray detector system 20, to enable image processing and/or image reconstruction by the image processing system 30.

By way of example, a conventional CT imaging system includes an X-ray source and an X-ray detector arranged in such a way that projection images of the subject or object can be acquired in different viewing angles covering at least 180 degrees. This is most commonly achieved by mounting the source and detector on a support, e.g., a rotating member of a gantry, that is able to rotate around the subject or object. An image containing the projections registered in the different detector elements for the different view angles is called a sinogram. In the following, a collection of projections registered in the different detector elements for different view angles will be referred to as a sinogram even if the detector is two-dimensional, making the sinogram a three-dimensional image.

FIG. 1B is a schematic diagram illustrating an example of an X-ray imaging system setup according to the prior art, showing projection lines from an X-ray source through an object to an X-ray detector.

A further development of X-ray imaging is energy-resolved X-ray imaging, also known as spectral X-ray imaging, where the X-ray transmission is measured for several different energy levels. This can be achieved by letting the source switch rapidly between two different emission spectra, by using two or more X-ray sources emitting different X-ray spectra, or by using an energy-discriminating detector which measures the incoming radiation in two or more energy levels. An example of such a detector is a multi-bin photon-counting detector, where each registered photon generates a current pulse which is compared to a set of thresholds, thereby counting the number of photons incident in each of a number of energy bins.

A spectral X-ray projection measurement results in a projection image for each energy level. A weighted sum of these projection images can be made to optimize the contrast-to-noise ratio (CNR) for a specified imaging task as described in "SNR and DQE analysis of broad spectrum X-ray imaging", Tapiovaara and Wagner, Phys. Med. Biol. 30, 519.

Another technique enabled by energy-resolved X-ray imaging is basis material decomposition. This technique utilizes the fact that all substances built up from elements with low atomic number, such as human tissue, have linear attenuation coefficients whose energy dependence can be expressed, to a good approximation, as a linear combination of two (or more) basis functions:

$$\mu(E) = \alpha_1 f_1(E) + \alpha_2 f_2(E)$$

where $f_1$ and $f_2$ are basis functions and $\alpha_1$ and $\alpha_2$ are the corresponding basis coefficients. More, generally, $f_1$ are basis functions and $\alpha_1$ are corresponding basis coefficients, where i=1, ..., N where N is the total number of basis functions. If there is one or more element in the imaged volume with high atomic number, high enough for a K-absorption edge to be present in the energy range used for the imaging, one basis function must be added for each such element. In the field of medical imaging, such K-edge elements can typically be iodine or gadolinium, substances that are used as contrast agents.

Basis material decomposition has been described in "Energy-selective reconstructions in X-ray computerized tomography", Alvarez, Macovski, Phys Med Biol. 1976; 21(5):733-744. In basis material decomposition, the integral of each of the basis coefficients, $A_i = \int_\ell \alpha_i dl$ for i=1, ..., N where N is the number of basis functions, is inferred from the measured data in each projection ray $\ell$ from the source to a detector element. In one implementation, this is accomplished by first expressing the expected registered number of counts in each energy bin as a function of $A_i$:

$$\lambda_i = \int_{E=0}^{\infty} S_i(E) \exp\left(-\sum_{j=1}^{N} A_j f_j(E)\right) dE$$

Here, $\lambda_i$ is the expected number of counts in energy bin i, E is the energy, $S_i$ is a response function which depends on the spectrum shape incident on the imaged object, the quantum efficiency of the detector and the sensitivity of energy bin i to X-rays with energy E. Even though the term "energy bin" is most commonly used for photon-counting detectors, this formula can also describe other energy resolving X-ray imaging systems such as multi-layer detectors or kVp switching sources.

Then, the maximum likelihood method may be used to estimate $A_i$, under the assumption that the number of counts in each bin is a Poisson distributed random variable. This is accomplished by minimizing the negative log-likelihood function, e.g., see "K-edge imaging in X-ray computed tomography using multi-bin photon counting detectors", Roessl and Proksa, Phys. Med. Biol. 52 (2007), 4679-4696:

$$\hat{A}_1, \ldots, \hat{A}_N = \underset{A_1, \ldots, A_N}{\operatorname{argmin}} \sum_{i=1}^{M_b} \lambda_i(A_1, \ldots, A_N) - m_i \ln \lambda_i(A_1, \ldots, A_N)$$

where $m_i$ is the number of measured counts in energy bin i and $M_b$ is the number of energy bins.

When the resulting estimated basis coefficient line integral $\hat{A}_i$ for each projection line is arranged into an image matrix, the result is a material specific projection image, also called a basis image, for each basis i. This basis image can either be viewed directly (e.g., in projection X-ray imaging) or taken as input to a reconstruction algorithm to form maps of basis coefficients $\alpha_1$ inside the object (e.g., in CT imaging). In either case, the result of a basis decomposition can be regarded as one or more basis image representations, such as the basis coefficient line integrals or the basis coefficients themselves.

CT imaging systems with a rotating section, such as a rotating member of a gantry, typically send all acquired data through data slip rings from the rotating section to a stationary computer, wherein the data is later processed in the stationary computer in order to reconstruct images of the subject or object.

Development in the CT imaging field makes increasingly high gantry rotation speeds and higher spatial resolution of the detectors possible; with this, the requirements for sufficiently handling the data increases.

As the amount of generated data is increased, a large burden is placed on the traditional CT imaging systems which are not designed for handling the increased data flows. Hence a limitation of the systems is that the large amount of data cannot be handled and transferred fast enough through the slip rings, resulting in e.g., a bottleneck effect which limits the use of the CT imaging system. This also holds true for similar X-ray imaging systems, where there is a need to transfer large amounts of data from a moving part or member of a gantry to a stationary part or member of the gantry.

Therefore, there is still a general demand for improvements with regard to data management in X-ray imaging systems such as CT systems.

SUMMARY

It is an object to mitigate, alleviate or eliminate one or more of the above-identified deficiencies in the art and disadvantages singly or in any combination and solve at least the above-mentioned problem.

It is a specific object to provide an improved X-ray imaging system.

It is also an object to provide a method of operating an X-ray imaging system.

Yet another object is to provide a corresponding computer program and computer-program product.

These and other objects are met by one or more embodiments of the present invention, as defined by the claims.

According to a first aspect there is provided an X-ray imaging system comprising a gantry including a moving part on a moving side and a stationary part on a stationary side, the moving part and the stationary part being communicatively coupled via a data communication system. The moving part comprises:

an X-ray source configured to emit X-rays;
an X-ray detector configured to generate detector data; and
on-moving-gantry processing circuitry.

The on-moving-gantry processing circuitry is configured to determine, for each of a number of partial data sets of the generated detector data, a metric value of at least one metric, the metric value being translatable into a type of data management for the partial data set among at least two different types of data management.

The on-moving-gantry processing circuitry is further configured to decide, for each partial data set, how the partial data set is to be treated in dependence on the determined metric value of said at least one metric and to selectively effectuate data management according to the corresponding type of data management.

In this way, the proposed technology shows how to build a high-performance X-ray imaging system within practical constraints based on a novel differential data treatment strategy.

In other words, efficient metric-based data management decisions can be made, e.g., to enable efficient handling of large amounts of detector data and/or to mitigate potential bottleneck effects in traditional X-ray imaging systems.

The term "moving" implies a member/section/segment that is movable, i.e. capable of moving or being moved relative to a stationary member/section/segment of the overall gantry.

The expression "on-moving-gantry" refers to the commonly used term "on-gantry" but more clearly specified as being related to the moving part of the gantry. More specifically, the expression "on-moving-gantry processing circuitry" refers to processing circuitry provided or arranged on the moving part of the gantry.

According to a second aspect there is provided a method of operating an X-ray imaging system having a gantry including a moving part on a moving side and a stationary part on a stationary side, the moving part and the stationary part being communicatively coupled via a data communication system. The moving part comprises an X-ray source configured to emit X-rays, an X-ray detector configured to generate detector data, and on-moving-gantry processing circuitry. The method comprises:

the X-ray detector generating detector data;
the on-moving-gantry processing circuitry determining, for each of a number of partial data sets of the generated detector data, a metric value of at least one metric based on the detector data of the partial data set;
the on-moving-gantry processing circuitry assigning a type of data management for the partial data set among at least two different types of data management in dependence on the determined metric value, and
the on-moving-gantry processing circuitry selectively effectuating data management for the partial data set according to the assigned type of data management.

According to a third aspect there is provided a computer-program product comprising a non-volatile computer-readable storage medium having stored thereon a computer program. The computer program comprises instructions, which when executed by processing circuitry arranged on a moving part of an X-ray imaging system, cause the processing circuitry to:

determine, for each of a number of partial data sets of detector data generated by an X-ray detector of the X-ray imaging system, a metric value of at least one metric based on the detector data of the partial data set;

assign a type of data management for the partial data set among at least two different types of data management in dependence on the determined metric value, selectively effectuate data management for the partial data set according to the assigned type of data management.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

For a better understanding, it may be useful to continue with an introductory description of non-limiting examples of an overall X-ray imaging system in which data processing and transferring according to the inventive concept may be implemented.

Figure 2:
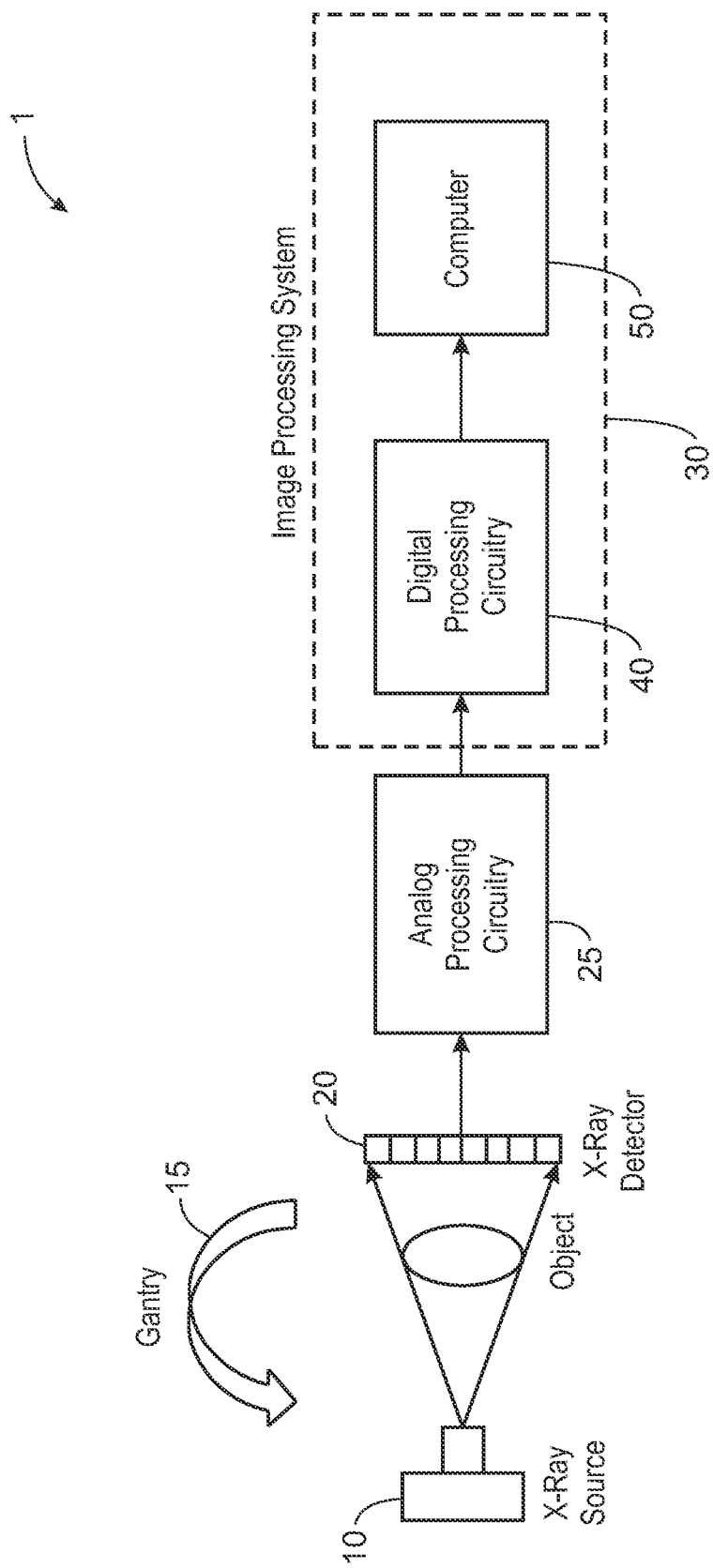
FIG. 2 is a schematic diagram illustrating another example of an X-ray imaging system, such as a CT imaging system.

FIG. 2 is a schematic diagram illustrating an example of an X-ray imaging system 1, such as a CT imaging system, comprising an X-ray source 10, which emits X-rays, an X-ray detector system 20 with an X-ray detector, which detects X-rays after they have passed through the object, analog processing circuitry 25, which processes the raw electrical signals from the X-ray detector and digitizes it, digital processing circuitry 40, which may carry out further processing operations on the measured data, such as applying corrections, storing it temporarily, or filtering, and a computer 50, which stores the processed data and may perform further post-processing and/or image reconstruction. According to an exemplary embodiment, all or part of the analog processing circuitry 25 may be implemented in the X-ray detector system 20. The X-ray source and X-ray detector may be coupled to a rotating member of a gantry 15 of the CT imaging system 1.

The overall X-ray detector may be regarded as the X-ray detector system 20, or the X-ray detector system 20 combined with the associated analog processing circuitry 25.

In communication with and electrically coupled to the analog processing circuitry 25 is an imaging processing system 30, which may include digital processing circuitry 40 and/or a computer 50, which may be configured to perform image reconstruction based on the image data from the X-ray detector. The image processing system 30 may, thus, be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used X-ray imaging system is a CT imaging system, which may include an X-ray source or X-ray tube that produces a fan beam or cone beam of X-rays and an opposing array of X-ray detectors measuring the fraction of X-rays that are transmitted through a patient or object. The X-ray source or X-ray tube and detector array are mounted in a gantry 15 that rotates around the imaged object.

Figure 3:
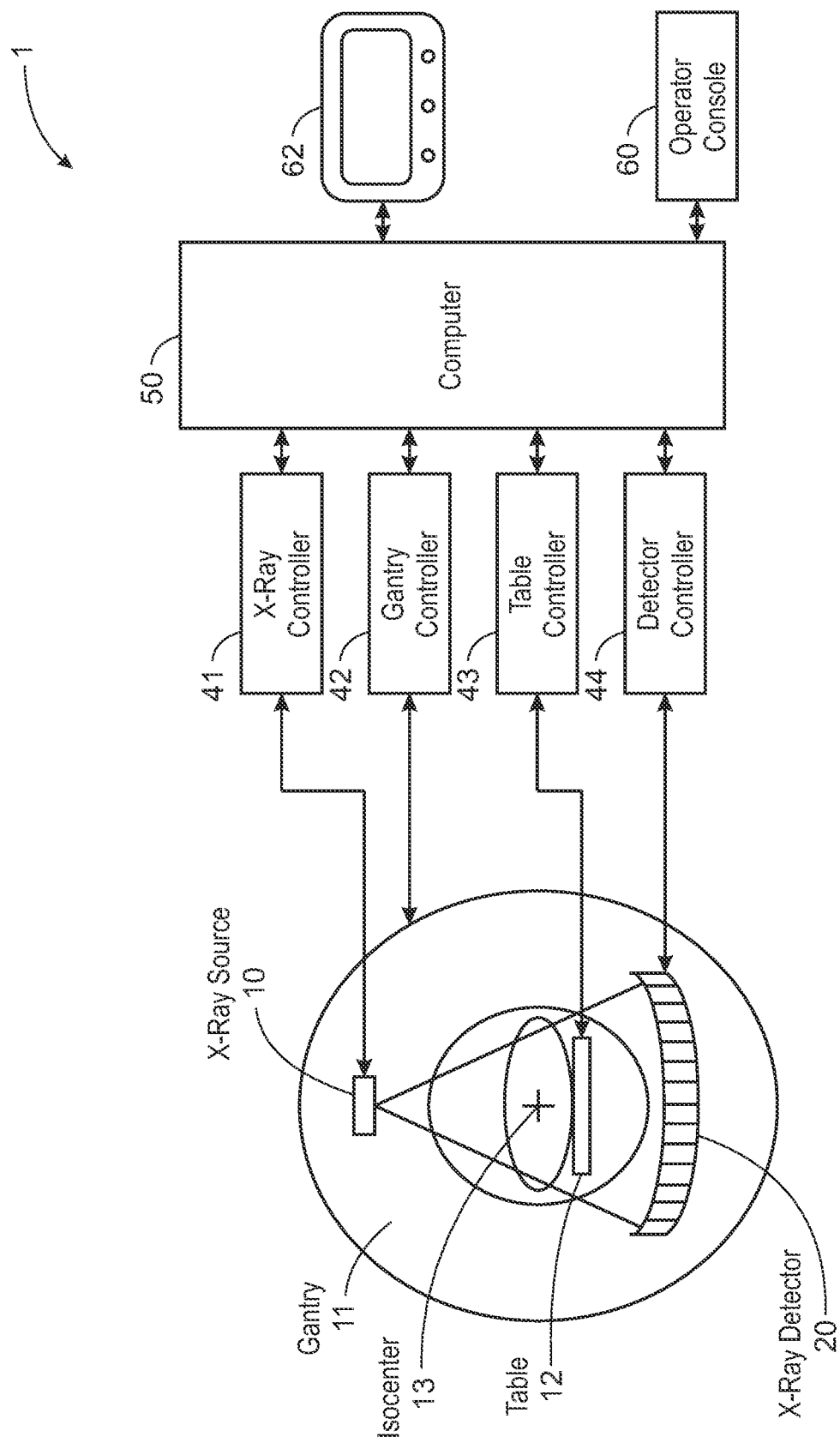
FIG. 3 is a schematic block diagram of a CT imaging system as an illustrative example of an X-ray imaging system.

FIG. 3 schematically shows a CT imaging system 1 as an illustrative example of an X-ray imaging system. The CT imaging system comprises a computer 50 receiving commands and scanning parameters from an operator via an operator console 60 that may have a display 62 and some form of operator interface, e.g., a keyboard, mouse, joy stick, touch screen or other input device. The operator supplied commands and parameters are then used by the computer 50 to provide control signals to an X-ray controller 41, a gantry controller 42 and a table controller 43. To be specific, the X-ray controller 41 provides power and timing signals to the x-ray source 10 to control emission of X-rays onto the object or patient lying on the table 12. The gantry controller 42 controls the rotating speed and position of the gantry 11 comprising the X-ray source 10 and the X-ray detector 20. By way of example, the X-ray detector 20 may be a photon-counting X-ray detector. The table controller 43 controls and determines the position of the patient table 12 and the scanning coverage of the patient. There is also a detector controller 44, which is configured for controlling and/or receiving data from the X-ray detector 20.

Figure 1A:
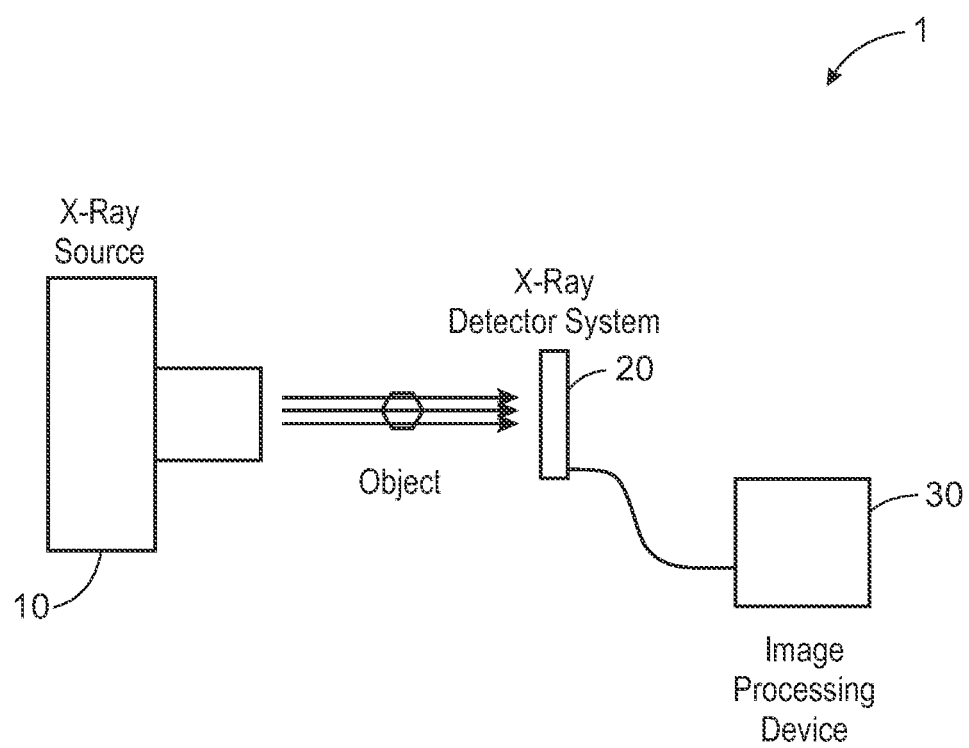
FIGS. 1A and B are schematic diagrams illustrating an example of an overall X-ray imaging system.
Figure 1B:
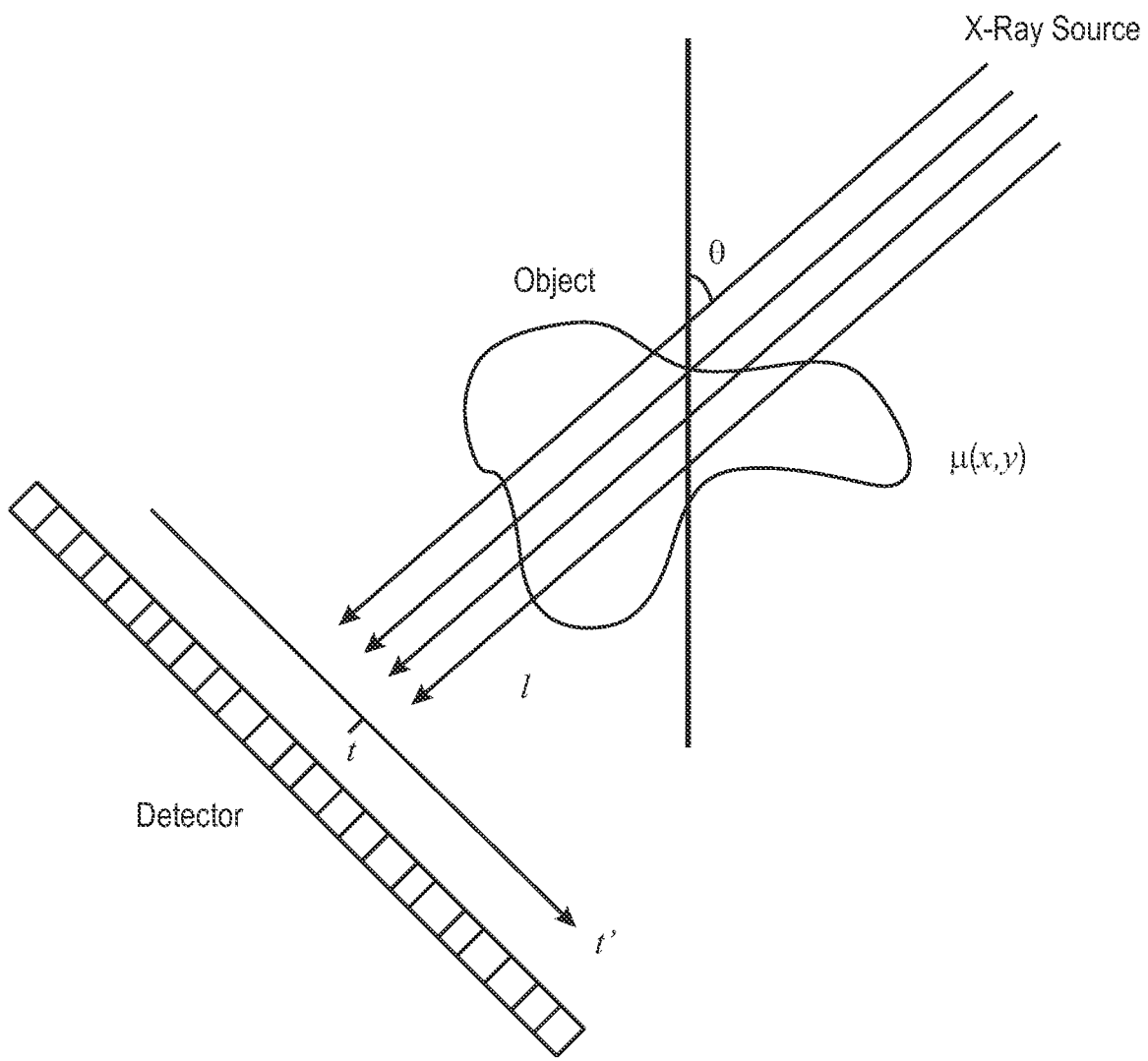

In an embodiment, the computer 50 also performs post-processing and image reconstruction of the image data output from the X-ray detector 20. The computer 50 thereby corresponds to the image processing system 30 as shown in FIGS. 1 and 2. The associated display 62 allows the operator to observe the reconstructed images and other data from the computer 50.

The X-ray source 10 arranged in the gantry 11 emits X-rays. An X-ray detector 20, which may be in the form of a photon-counting X-ray detector, detects the X-rays after they have passed through the object or patient. The X-ray detector 20 may for example be formed by plurality of pixels, also referred to as sensors or detector elements, and associated processing circuitry, such as Application Specific Integrated Circuits (ASICs), arranged in detector modules. A portion of the analog processing part may be implemented in the pixels, whereas any remaining processing part is implemented in, for instance, the ASICs. In an embodiment, the processing circuitry (ASICs) digitizes the analog signals from the pixels. The processing circuitry (ASICs) may also comprise a digital processing part, which may carry out further processing operations on the measured data, such as applying corrections, storing it temporarily, and/or filtering. During a scan to acquire X-ray projection data, the gantry and the components mounted thereon rotate about an iso-center 13.

Modern X-ray detectors normally need to convert the incident X-rays into electrons, this typically takes place through the photoelectric effect or through Compton interaction and the resulting electrons are usually creating secondary visible light until its energy is lost and this light is in turn detected by a photo-sensitive material. There are also detectors, which are based on semiconductors and in this case the electrons created by the X-ray are creating electric charge in terms of electron-hole pairs which are collected through an applied electric field.

There are detectors operating in an energy integrating mode in the sense that they provide an integrated signal from a multitude of X-rays. The output signal is proportional to the total energy deposited by the detected X-rays.

X-ray detectors with photon counting and energy resolving capabilities are becoming common for medical X-ray applications. The photon counting detectors have an advantage since in principle the energy for each X-ray can be measured which yields additional information about the composition of the object. This information can be used to increase the image quality and/or to decrease the radiation dose.

Generally, a photon-counting X-ray detector determines the energy of a photon by comparing the height of the electric pulse generated by a photon interaction in the detector material to a set of comparator voltages. These comparator voltages are also referred to as energy thresholds. Generally, the analog voltage in a comparator is set by a digital-to-analog converter (DAC). The DAC converts a digital setting sent by a controller to an analog voltage with respect to which the heights of the photon pulses can be compared.

A photon-counting detector counts the number of photons that have interacted in the detector during a measurement time. A new photon is generally identified by the fact that the height of the electric pulse exceeds the comparator voltage of at least one comparator. When a photon is identified, the event is stored by incrementing a digital counter associated with the channel.

When using several different threshold values, a so-called energy-discriminating photon-counting detector is obtained, in which the detected photons can be sorted into energy bins corresponding to the various threshold values. Sometimes, this type of photon-counting detector is also referred to as a multi-bin detector. In general, the energy information allows for new kinds of images to be created, where new information is available and image artifacts inherent to conventional technology can be removed. In other words, for an energy-discriminating photon-counting detector, the pulse heights are compared to a number of programmable thresholds (Ti-TN) in the comparators and are classified according to pulse-height, which in turn is proportional to energy. In other words, a photon counting detector comprising more than one comparator is here referred to as a multi-bin photon counting detector. In the case of multi-bin photon counting detector, the photon counts are stored in a set of counters, typically one for each energy threshold. For example, counters can be assigned to correspond to the highest energy threshold that the photon pulse has exceeded. In another example, counters keep track of the number of times that the photon pulse cross each energy threshold.

As an example, edge-on is a special, non-limiting design for a photon-counting detector, where the X-ray sensors such as X-ray detector elements or pixels are oriented edge-on to incoming X-rays.

For example, such photon-counting detectors may have pixels in at least two directions, wherein one of the directions of the edge-on photon-counting detector has a component in the direction of the X-rays. Such an edge-on photon-counting detector is sometimes referred to as a depth-segmented photon-counting detector, having two or more depth segments of pixels in the direction of the incoming X-rays.

Alternatively, the pixels may be arranged as an array (non-depth-segmented) in a direction substantially orthogonal to the direction of the incident X-rays, and each of the pixels may be oriented edge-on to the incident X-rays. In other words, the photon-counting detector may be non-depth-segmented, while still arranged edge-on to the incoming X-rays.

By arranging the edge-on photon-counting detector edge-on, the absorption efficiency can be increased, in which case the absorption depth can be chosen to any length, and the edge-on photon-counting detector can still be fully depleted without going to very high voltages.

A conventional mechanism to detect X-ray photons through a direct semiconductor detector basically works as follows. The energy of the X-ray interactions in the detector material are converted to electron-hole pairs inside the semiconductor detector, where the number of electron-hole pairs is generally proportional to the photon energy. The electrons and holes are drifted towards the detector electrodes and backside (or vice versa). During this drift, the electrons and holes induce an electrical current in the electrode, a current which may be measured.

Figure 4:
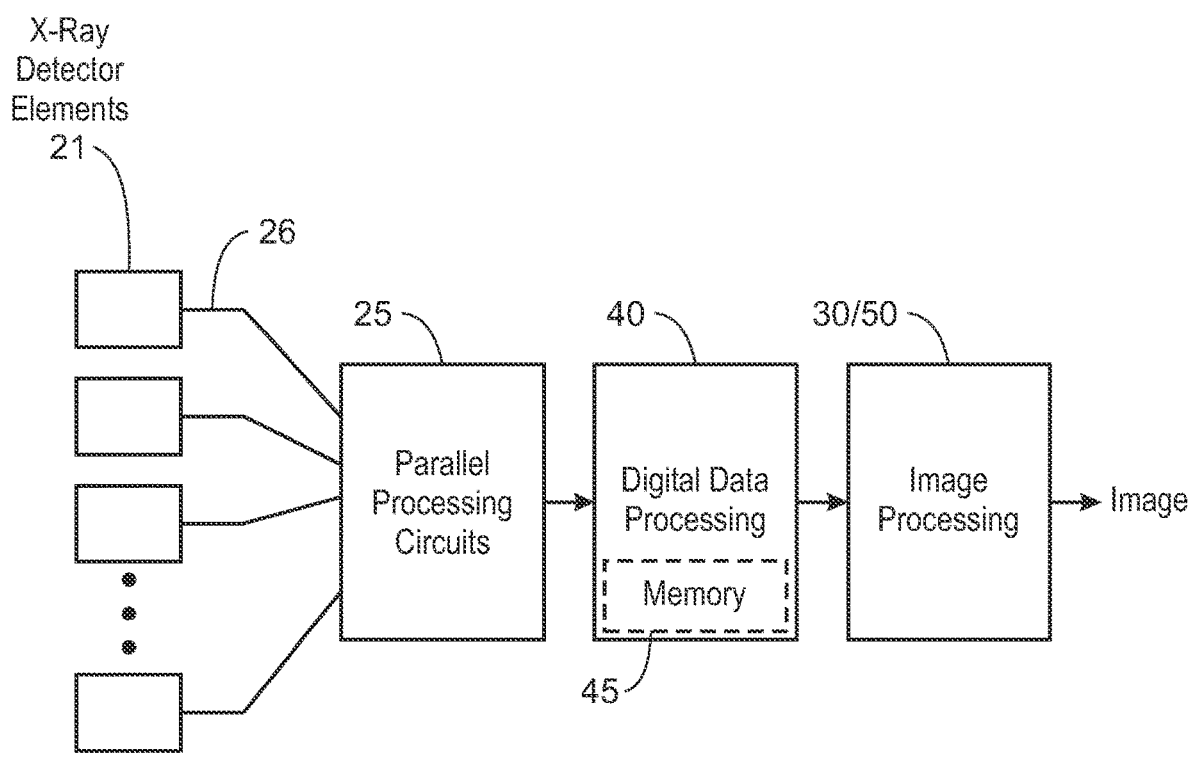
FIG. 4 is a schematic diagram illustrating another example of relevant parts of an X-ray imaging system, such as a CT imaging system.

As illustrated in FIG. 4, signal(s) is/are routed 26 from detector elements 22 of the X-ray detector to inputs of parallel processing circuits (e.g., ASICs) 25. It should be understood that the term Application Specific Integrated Circuit (ASIC) is to be interpreted broadly as any general circuit used and configured for a specific application. The ASIC processes the electric charge generated from each X-ray and converts it to digital data, which can be used to obtain measurement data such as a photon count and/or estimated energy. The ASICs are configured for connection to digital data processing circuitry so the digital data may be sent to further digital data processing 40 and/or one or more memory circuits or components 45 and finally the data will be the input for image processing 30/50 to generate a reconstructed image.

As the number of electrons and holes from one X-ray event is proportional to the energy of the X-ray photon, the total charge in one induced current pulse is proportional to this energy. After a filtering step in the ASIC, the pulse amplitude is proportional to the total charge in the current pulse, and therefore proportional to the X-ray energy. The pulse amplitude can then be measured by comparing its value with one or more thresholds (THR) in one or more comparators (COMP), and counters are introduced by which the number of cases when a pulse is larger than the threshold value may be recorded. In this way it is possible to count and/or record the number of X-ray photons with an energy exceeding an energy corresponding to respective threshold value (THR) which has been detected within a certain time frame.

The ASIC typically samples the analog photon pulse once every Clock Cycle and registers the output of the comparators. The comparator(s) (threshold) outputs a one or a zero depending on whether the analog signal was above or below the comparator voltage. The available information at each sample is, for example, a one or a zero for each comparator representing weather the comparator has been triggered (photon pulse was higher than the threshold) or not.

In a photon counting detector, there is typically a Photon Counting Logic which determines if a new photon has been registered and, registers the photons in counter(s). In the case of a multi-bin photon counting detector, there are typically several counters, for example one for each comparator, and the photon counts are registered in the counters in accordance with an estimate of the photon energy. The logic can be implemented in several different ways. Two of the most common categories of Photon Counting Logic are the so-called non-paralyzable counting modes, and the paralyzable counting modes. Other photon-counting logics include, for example, local maxima detection, which counts, and possibly also registers the pulse height of, detected local maxima in the voltage pulse.

There are many benefits of photon-counting detectors including, but not limited to: high spatial resolution; less sensitivity to electronic noise; good energy resolution; and material separation capability (spectral imaging ability). However, energy integrating detectors have the advantage of high count-rate tolerance. The count-rate tolerance comes from the fact/recognition that, since the total energy of the photons is measured, adding one additional photon will always increase the output signal (within reasonable limits), regardless of the amount of photons that are currently being registered by the detector. This advantage is one of the main reasons that energy integrating detectors are the standard for medical CT today.

Figure 5:
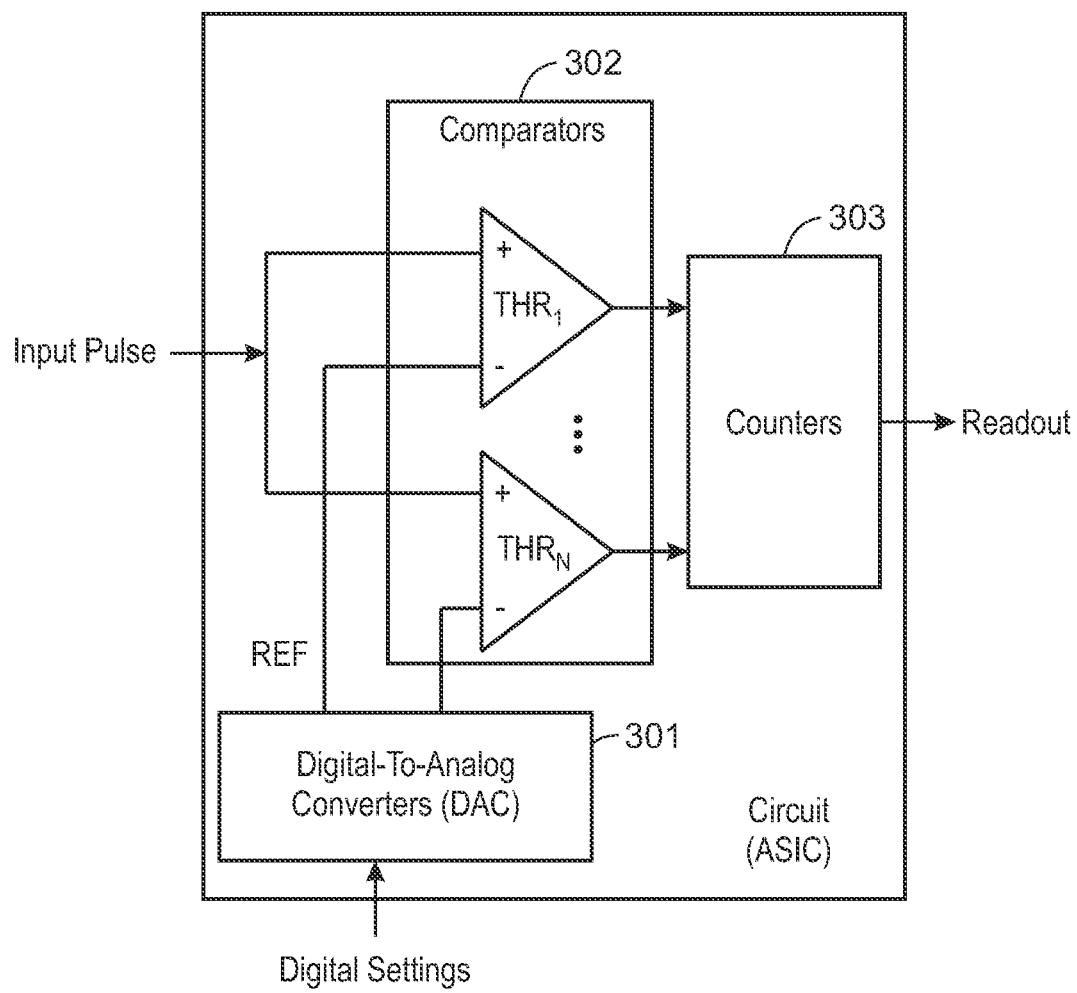
FIG. 5 is a schematic illustration of a photon-counting circuit and/or device according to prior art.

FIG. 5 shows a schematic illustration of a photon-counting circuit and/or device according to prior art.

When a photon interacts in a semiconductor material, a cloud of electron-hole pairs is created. By applying an electric field over the detector material, the charge carriers are collected by electrodes attached to the detector material. The signal is routed from the detector elements to inputs of parallel processing circuits, e.g., ASICs. It should be understood that the term Application Specific Integrated Circuit, ASIC, is to be interpreted broadly as any general circuit used and configured for a specific application. The ASIC processes the electric charge generated from each X-ray and converts it to digital data, which can be used to obtain measurement data such as a photon count and/or estimated energy. In one example, the ASIC can process the electric charge such that a voltage pulse is produced with maximum height proportional to the amount of energy deposited by the photon in the detector material.

The ASIC may include a set of comparators 302 where each comparator 302 compares the magnitude of the voltage pulse to a reference voltage. The comparator output is typically zero or one (0/1) depending on which of the two compared voltages that is larger. Here we will assume that the comparator output is one (1) if the voltage pulse is higher than the reference voltage, and zero (0) if the reference voltage is higher than the voltage pulse. Digital-to-analog converters (DACs), 301 can be used to convert digital settings, which may be supplied by the user or a control program, to reference voltages that can be used by the comparators 302. If the height of the voltage pulse exceeds the reference voltage of a specific comparator, we will refer to the comparator as triggered. Each comparator is generally associated with a digital counter 303, which is incremented based on the comparator output in accordance with the photon counting logic.

As previously mentioned, when the resulting estimated basis coefficient line integral $\hat{A}_i$ for each projection line is arranged into an image matrix, the result is a material specific projection image, also called a basis image, for each basis i. This basis image can either be viewed directly (e.g., in projection X-ray imaging) or taken as input to a reconstruction algorithm to form maps of basis coefficients $\alpha_1$ inside the object (e.g., in CT). Anyway, the result of a basis decomposition can be regarded as one or more basis image representations, such as the basis coefficient line integrals or the basis coefficients themselves.

It will be appreciated that the mechanisms and arrangements described herein can be implemented, combined and re-arranged in a variety of ways.

For example, embodiments may be implemented in hardware, or at least partly in software for execution by suitable processing circuitry, or a combination thereof.

The steps, functions, procedures, and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, and/or blocks described herein may be implemented in software such as a computer program for execution by suitable processing circuitry such as one or more processors or processing units.

In the following, non-limiting examples of specific detector module implementations will be discussed. More particularly, these examples refer to edge-on oriented detector modules and depth-segmented detector modules. Other types of detectors and detector modules may also be feasible.

Figure 6:
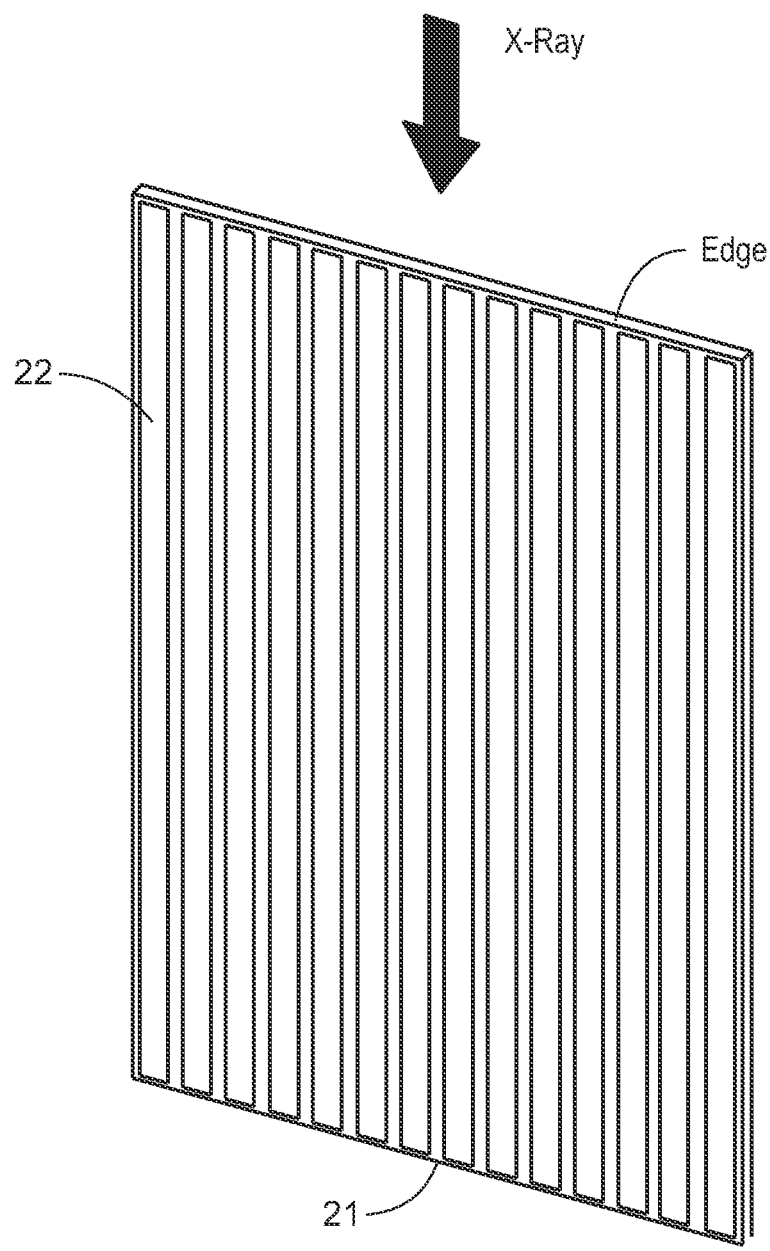
FIG. 6 is a schematic diagram illustrating an example of a semiconductor detector sub-module according to an exemplary embodiment.

FIG. 6 is a schematic diagram illustrating an example of a semiconductor detector sub-module according to an exemplary embodiment. This is an example of a semiconductor detector sub-module with the semiconductor sensor 21 split into detector elements or pixels 22, where each detector element (or pixel) is normally based on a diode having a charge collecting electrode as a key component. The X-rays enter through the edge of the semiconductor sensor.

Figure 7:
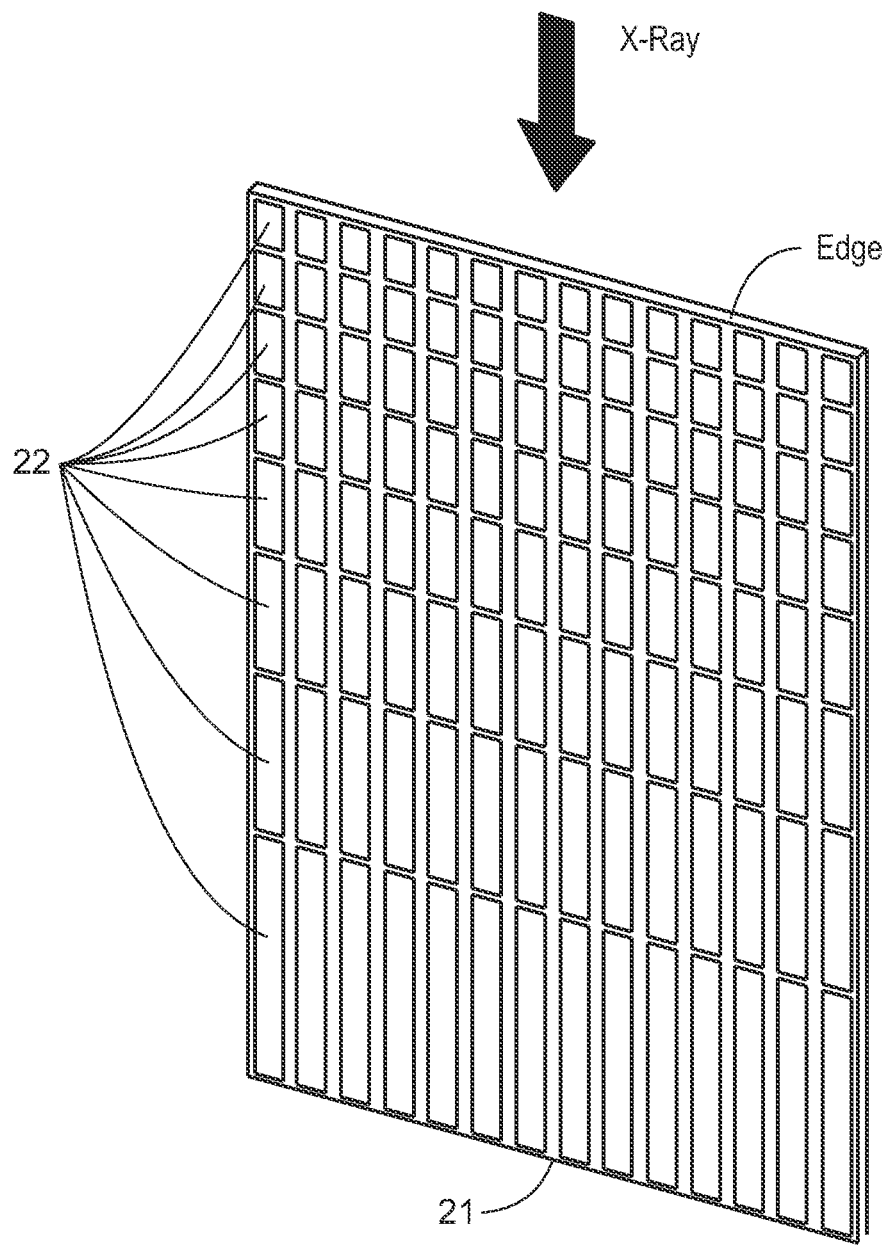
FIG. 7 is a schematic diagram illustrating an example of semiconductor detector sub-module according to another exemplary embodiment.

FIG. 7 is a schematic diagram illustrating an example of semiconductor detector sub-module according to another exemplary embodiment. In this example, the semiconductor sensor 21 is also split into a plurality of so-called depth segments or detector elements 22 in the depth direction, again assuming the X-rays enter through the edge.

Normally, a detector element is an individual X-ray sensitive sub-element of the detector. In general, the photon interaction takes place in a detector element and the thus generated charge is collected by the corresponding electrode of the detector element.

Each detector element typically measures the incident X-ray flux as a sequence of frames. A frame is the measured data during a specified time interval, called frame time.

Depending on the detector topology, a detector element may correspond to a pixel, especially when the detector is a flat-panel detector. A depth-segmented detector may be regarded as having a number of detector strips, each strip having a number of depth segments. For such a depth-segmented detector, each depth segment may be regarded as an individual detector element, especially if each of the depth segments is associated with its own individual charge collecting electrode.

The detector strips of a depth-segmented detector normally correspond to the pixels of an ordinary flat-panel detector, and therefore sometimes also referred to as pixel strips. However, it is also possible to regard a depth-segmented detector as a three-dimensional pixel array, where each pixel (sometimes referred to as a voxel) corresponds to an individual depth segment/detector element.

The semiconductor sensors may be implemented as so called Multi-Chip Modules (MCMs) in the sense that the semiconductor sensors are used as base substrates for electric routing and for a number of ASICs which are attached preferably through so called flip-chip technique. The routing will include a connection for the signal from each pixel or detector element to the ASIC input as well as connections from the ASIC to external memory and/or digital data processing. Power to the ASICs may be provided through similar routing taking into account the increase in cross-section which is required for the large currents in these connections, but the power may also be provided through a separate connection. The ASICS may be positioned on the side of the active sensor and this means it can be protected from the incident X-rays if an absorbing cover is placed on top and it can also be protected from scattered X-rays from the side by positioning an absorber also in this direction.

Figure 8B:
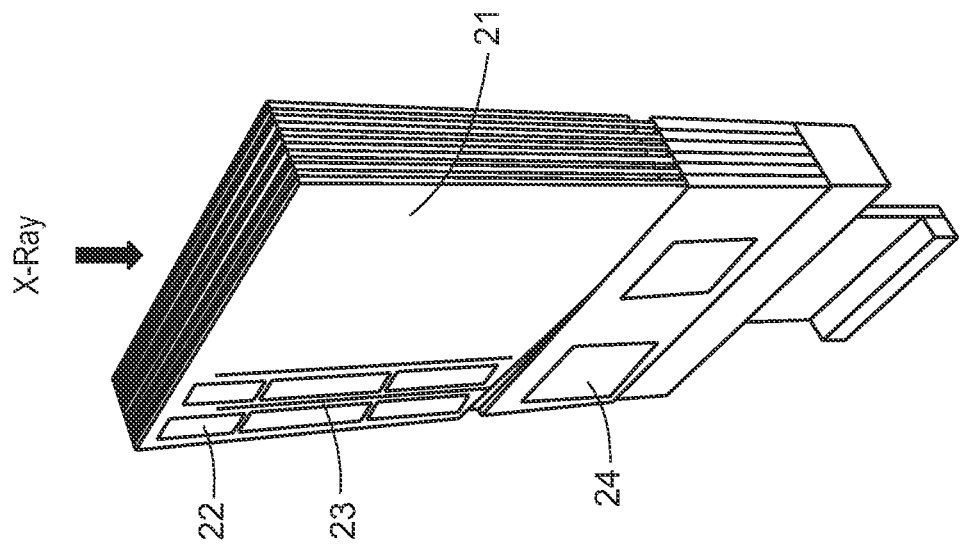
FIG. 8B is a schematic diagram illustrating an example of a set of tiled detector sub-modules, where each detector sub-module is a depth-segmented detector sub-module and the Application Specific Integrated Circuits (ASICs) or corresponding circuitry are arranged below the detector elements as seen from the direction of the incoming X-rays.
Figure 8A:
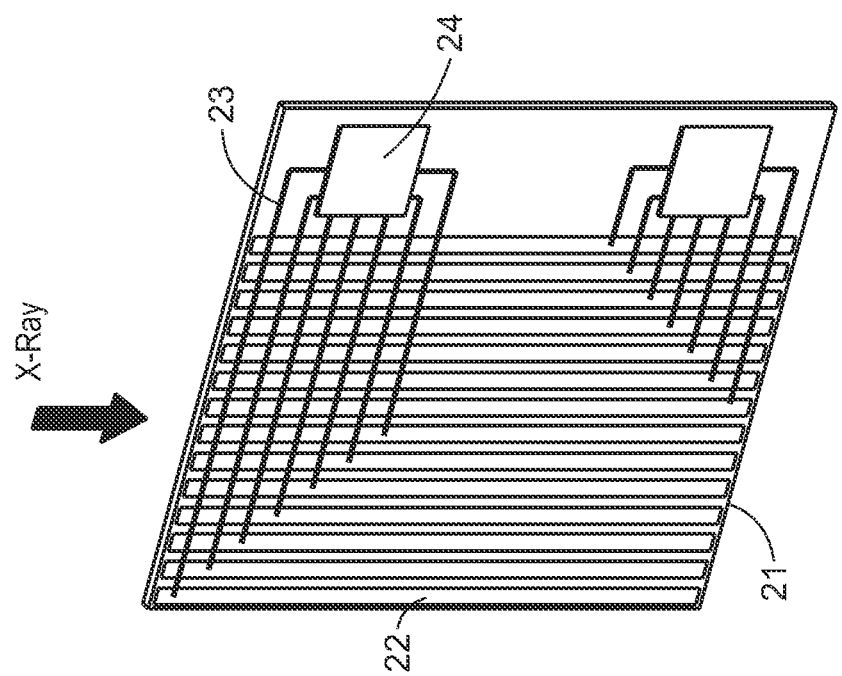
FIG. 8A is a schematic diagram illustrating an example of a semiconductor detector sub-module according to yet another exemplary embodiment.

FIG. 8A is a schematic diagram illustrating a semiconductor detector sub-module implemented as a MCM similar to embodiments in U.S. Pat. No. 8,183,535. In this example, it is illustrated how the semiconductor sensor 21 also can have the function of substrate in a MCM. The signal is routed by signal paths 23 from the detector elements or pixels 22 to inputs of parallel processing circuits 24 (e.g., ASICs) that are positioned next to the active sensor area. It should be understood that the term Application Specific Integrated Circuit (ASIC) is to be interpreted broadly as any general integrated circuit used and configured for a specific application. The ASICs process the electric charge generated from each X-ray and converts it to digital data which can be used to detect a photon and/or estimate the energy of the photon. The ASICs may have their own digital processing circuitry and memory for small tasks. And, the ASICs may be configured for connection to digital processing circuitry and/or memory circuits or components located outside of the MCM and finally the data will be used as input for reconstructing an image.

However, the employment of depth segments also brings two noticeable challenges to a silicon-based photon-counting detector. First, a large number of ASIC channels has to be employed to process data fed from the associated detector segments. In addition to the increased number of channels due to both the smaller pixel size and the depth segmentation, multi-energy bin further increases the data size. Second, since the given X-ray input counts are divided into smaller pixels, segments and energy bins, each bin has much lower signal and so the detector calibration/correction requires more than several orders of magnitude more calibration data to minimize statistical uncertainty.

Naturally, the several orders of magnitude larger data size slow down both data handling and pre-processing in addition to the need of larger computing resources, harddisk, memory and central processing unit (CPU)/graphics processing unit (GPU). When the size of data is 10 Gigabytes instead of 10 Megabyte, for example, the data handling time, read and write, can take 1000 times longer.

A problem in any counting X-ray photon detector is the so-called pile-up problem. When the flux rate of X-ray photons is high there may be problems in distinguishing between two subsequent charge pulses. As mentioned above, the pulse length after the filter depends on the shaping time. If this pulse length is larger than the time between two X-ray photon induced charge pulses, the pulses will grow together, and the two photons are not distinguishable and may be counted as one pulse. This is called pile-up. One way to avoid pile-up at high photon flux is thus to use a small shaping time, or to use depth-segmentation.

For pileup calibration vector generation, the pileup calibration data needs to be pre-processed for spit correction. For material decomposition vector generation, the material decomposition data needs to be pre-processed for both spit and pileup correction. For patient scan data, the data needs to be pre-processed for spit, pileup and material decomposition before the image reconstruction ensues. These are simplified examples to explain "pre-processing" since the actual pre-processing steps can include several other calibration steps as needed, like reference normalization and air calibration. The term "processing" may indicate only the final step in each calibration vector generation or patient scan, but it is used interchangeably in some cases.

FIG. 8B is a schematic diagram illustrating an example of a set of tiled detector sub-modules, where each detector sub-module is a depth-segmented detector sub-module and the ASICs or corresponding circuitry 24 are arranged below the detector elements 22 as seen from the direction of the incoming X-rays, allowing for routing paths from the detector elements 22 to the ASICs 23 in the space between detector elements.

The present invention relates to a novel system architecture and corresponding procedures for improved data management for X-ray imaging systems such as CT systems.

According to a first aspect there is provided an X-ray imaging system comprising a gantry including a moving part on a moving side and a stationary part on a stationary side, the moving part and the stationary part being communicatively coupled via a data communication system. The moving part comprises:
an X-ray source configured to emit X-rays;
an X-ray detector configured to generate detector data; and
on-moving-gantry processing circuitry.

The on-moving-gantry processing circuitry is configured to determine, for each of a number of partial data sets of the generated detector data, a metric value of at least one metric, the metric value being translatable into a type of data management for the partial data set among at least two different types of data management.

The on-moving-gantry processing circuitry is further configured to decide, for each partial data set, how the partial data set is to be treated in dependence on the determined metric value of said at least one metric and to selectively effectuate data management according to the corresponding type of data management.

The proposed technology enables efficient metric-based data management decisions to be made, e.g., to enable efficient handling of large amounts of detector data and/or to mitigate potential bottleneck effects in traditional X-ray imaging systems.

In this way, the proposed technology makes it possible to more optimally exploit the superior imaging potential of modern X-ray detectors such as high-resolution, photon-counting, interferometric (e.g., phase contrast and dark field imaging), energy-discriminating and/or multi-segment detectors.

Thus, the proposed technology effectively handles the tradeoff between data fidelity and practical constraints related to computational resources, electrical power, cooling, space and/or data transfer bandwidth.

The term "moving" implies a member/section/segment that is movable, i.e. capable of moving or being moved relative to a stationary member/section/segment of the overall gantry.

The expression "on-moving-gantry" refers to the commonly used term "on-gantry" but more clearly specified as being related to the moving part of the gantry. More specifically, the expression "on-moving-gantry processing circuitry" refers to processing circuitry provided or arranged on the moving part of the gantry.

By way of example, the X-ray imaging system may be a Computed Tomography (CT) system, and the moving part and the stationary part may be a rotating part and a stationary part of the gantry of the CT system.

For example, the rotating part may be a rotating member/section/segment of the CT gantry, which is configured to rotate, e.g., around the subject/object to be imaged. The stationary part may be defined as a stationary member/section/segment of the CT gantry, which is arranged in a stationary manner on the stationary side, wherein the rotating part and the stationary part may be communicatively connected via a data communication system, e.g., one or more slip rings. In the particular example of a CT system, the expression "on-moving-gantry processing circuitry" refers to processing circuitry provided or arranged on the rotating part of the gantry.

The expression, "off-moving-gantry data processing" implies that the data processing is lifted "off" the moving part of the gantry and is performed on the stationary side by processing circuitry arranged or provided on the stationary part of the overall gantry.

Figure 9:
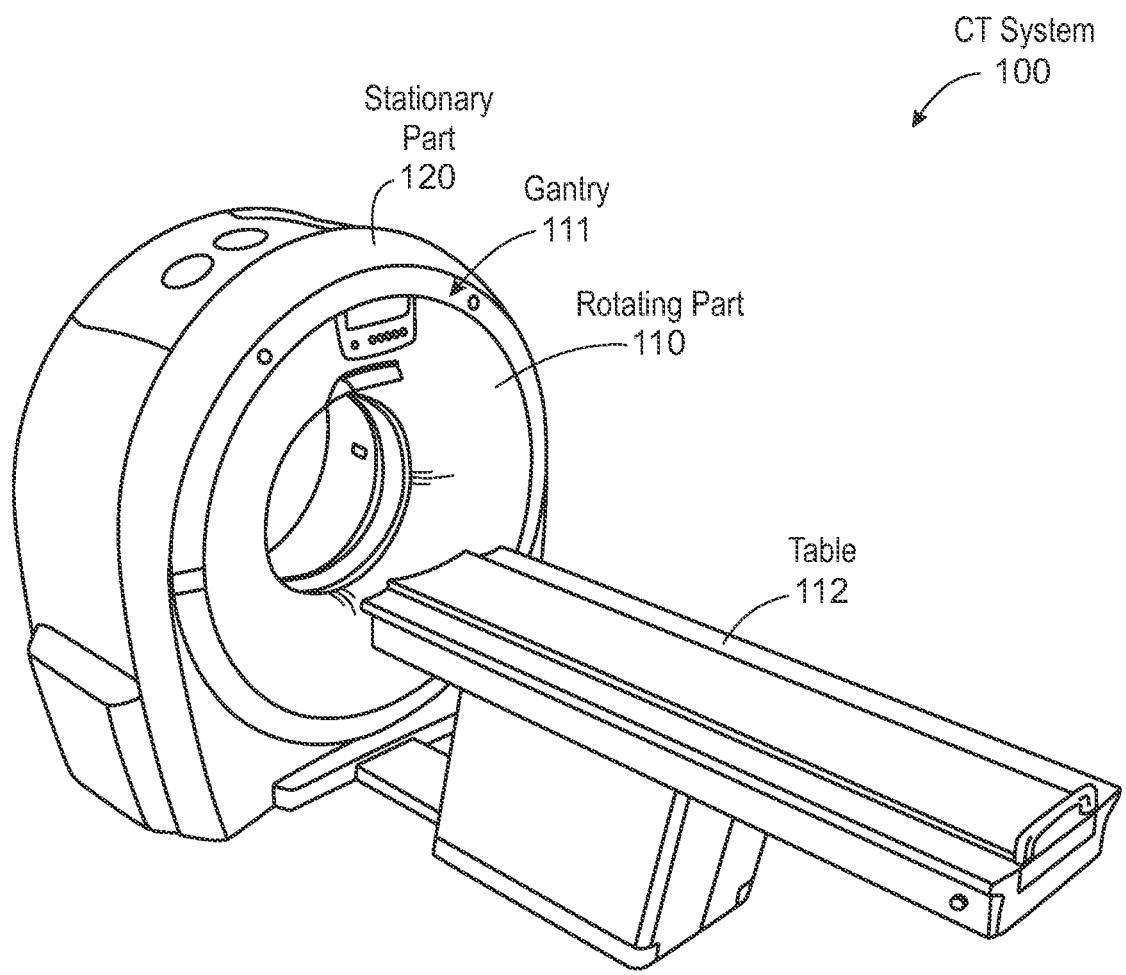
FIG. 9 is a schematic diagram illustrating an overview example of a CT imaging system.

FIG. 9 is a schematic diagram illustrating an overview example of a CT imaging system. In this schematic example, the overall CT system 100 comprises a gantry 111 having a rotating part 110 on a rotating side and a stationary part 120 on a stationary side. The CT system further includes a standard patient table 112 that can be inserted into the opening of the gantry 111 during a patient scan and/or a calibration scan.

It should though be understood that the moving part and the stationary part of the gantry do not have to be part of a CT system, but may be arranged and/or configured in other ways, e.g., for linear and/or translative relative movement without rotation. As an example, the X-ray source and detector combination may be moved relative to a stationary part of the overall gantry in a linear and/or translative manner. For example, the X-ray source and detector may be moved together as an aggregate assembly unit along the table axis, commonly referred to as the z-axis. Alternatively, the patient table is moved, while the X-ray source and detector combination stands still; the relative movement is the key. This also includes geometric system configurations where the patient may be standing, e.g., in a so-called phone booth type scanner.

In a particular example, the on-moving-gantry processing circuitry is configured to identify at least two different partial data sets of the generated detector data for which different types of data management are to be applied.

In this way, robust and efficient multimode partial data set management may be achieved, where intelligent metric-based data management decisions can be made.

For example, the at least two different types of data management may include at least one of the following:
i) performing on-moving-gantry data processing of the partial data set of the generated detector data before transmission of the partial data set from the moving part to the stationary part,
ii) performing no on-moving-gantry data processing of the partial data set of the generated detector data before transmission of the partial data set from the moving part to the stationary part, and
iii) omitting transmission of the partial data set of the generated detector data.

In a particular example, on-moving-gantry processing circuitry may be further configured to perform on-moving-gantry data processing of different levels of computational complexity for different partial data sets.

By way of example, the on-moving-gantry processing circuitry may be configured to decide, based on the determined metric value of said at least one metric for a first partial data set, that on-moving-gantry data processing of the first partial data set is to be applied before transmission from the moving part to the stationary part. The on-moving-gantry processing circuitry may be configured to decide, based on the determined metric value of said at least one metric for a second partial data set, that the second partial data set is to be transmitted from the moving part to the stationary part without on-moving-gantry data processing, or that on-moving-gantry data processing of a lower level of computational complexity than for the first partial data set is to be applied to the second partial data set before transmission from the moving part to the stationary part.

For example, the on-moving-gantry processing circuitry may be configured to perform on-moving-gantry data processing of the first partial data set by data reduction to generate a reduced first partial data set for transmission from the moving part to the stationary part.

Optionally, the X-ray imaging system further comprises additional processing circuitry in connection with the stationary part, the additional processing circuitry being configured to perform a material decomposition procedure adapted for the reduced first partial data set.

As another example, the on-moving-gantry processing circuitry may be configured to decide, based on the determined metric value of said at least one metric for a specific partial data set, that the specific partial data set is to be omitted from transmission from the moving part to the stationary part.

In a particular example embodiment, the on-moving-gantry processing circuitry may be configured to determine in which one of at least two non-overlapping intervals the determined metric value of said at least one metric resides, each interval being associated with a respective one of the at least two different types of data management, to thereby enable associating the determined metric value with a specific type of data management for the considered partial data set.

It should be clear that the measured detector data may be characterized or represented by one or more metrics. The metrics may be designed to be representative of one or more properties of the measured data. Non-limiting examples of metrics may include representations of the signal-to-noise ratio of the measured data, the contrast-to-noise ratio of the data, the autocorrelation of the data, the cross-correlation of the data, the mean value of the data, the estimated thicknesses through which the rays that contributed the data traveled, the degree of pulse pile-up present in the data, the statistical distribution of the data, the results of hypothesis tests on the data. By way of example, metrics may be based on the frequency content of projections measurements, both temporal and spatial. For example, edge features may be detected to enable differential processing for detector crosstalk correction. Metrics may apply directly to the data or to linear or non-linear transformations of the data. Metrics may take into account imaging parameters such as kVp, tube mA. Metrics may also take into account prior information about the imaged object. For example, metrics may take into account models of the source (e.g., spectrum, focal spot shape, focal spot size) and/or the detector (e.g., energy response, pile-up response, crosstalk).

In a particular example, said at least one metric may include a pileup metric representing an amount of pulse pileup within at least part of the considered partial data set of the generated detector data, and the on-moving-gantry processing circuitry may be configured to decide, in dependence on the determined metric value of the pileup metric, whether on-moving-gantry pile-up correction data processing is to be applied to the partial data set and to selectively effectuate this on-moving-gantry pile-up correction data processing of the partial data set to generate a corrected data set.

Optionally, additional off-moving-gantry pile-up correction data processing of the corrected data set may be performed by processing circuitry on the stationary part.

For example, the on-moving-gantry processing circuitry may be configured to perform on-moving-gantry pile-up correction data processing when the determined metric value of the pile-up metric indicates an amount of pile-up that is higher than zero but lower than a first threshold level.

In an optional embodiment, the on-moving-gantry processing circuitry may be configured to decide that the partial data set is to be transmitted from the moving part to the stationary part without on-moving-gantry pileup correction data processing when the determined metric value of the pileup metric indicates an amount of pileup that is higher than a second threshold level.

For example, off-moving-gantry pileup correction data processing of the partial data set may be performed by processing circuitry on the stationary part.

In a particular example, the on-moving-gantry processing circuitry is configured to determine the pileup metric based on a comparison between estimated true photon counts and measured photon counts. For example, the on-gantry processing circuitry may be configured to determine the pileup metric based on a ratio or difference between estimated (true) photon counts and measured photon counts. Such a ratio or difference may be determined, e.g., per detector pixel or for a group of detector pixels, for at least a subset of pixel sub-elements, and/or over at least a subset of energy bins. By way of example, the estimate of the true photon counts can be determined as a weighted combination of counts under certain biasing assumptions. Typically, photon counts that should appear in a certain energy bin instead appear in a higher energy bin (biased higher). The dominant pileup effect is normally the summing of the energies of several apparently coincident photons. The measured energy is therefore biased higher, and the photon count is biased lower, relative to truth (i.e. the true physical interactions actually occurring in the detector).

In another example embodiment, said at least one metric includes an X-ray propagation metric or X-ray attenuation metric.

For example, the on-moving-gantry processing circuitry may be configured to identify a partial data set in which the detector data corresponds to X-rays travelling exclusively through air from the X-ray source the X-ray detector based on the X-ray propagation metric or X-ray attenuation metric, and the on-moving-gantry processing circuitry may then be configured to decide that the identified partial data set is to be omitted from transmission from the moving part to the stationary part.

Typically, each partial data set may correspond to a batch of the generated detector data that is related to an X-ray measurement or a group of X-ray measurements.

Optionally, the data communication system is configured to transmit, for at least one partial data set, a representation of the corresponding determined metric value, or an identifier representing the type of applied data management, from the moving part to the stationary part in association with the partial data set.

For example, the identifier may indicate whether on-moving-gantry data processing of the partial data set has been performed.

As an example, the data communication system may comprise a first data communication unit on the moving part on the moving side and a second data communication unit on the stationary part on the stationary side. This could be, e.g., one or more slip rings for a CT system.

Additionally, the moving part may comprise an on-moving-gantry data storage unit in connection with the on-moving-gantry processing circuitry for storage of the detector data in processed and/or unprocessed form, as will be exemplified later on.

By way of example, the X-ray detector is a photon-counting detector.

As previously explained, the X-ray imaging system may be a Computed Tomography (CT) system, and the moving part and the stationary part may be a rotating part and a stationary part of the gantry of the CT system, e.g., as schematically illustrated in FIG. 9. However, the proposed technology is not limited thereto. Alternatively, or as a complement, the moving part and the stationary part of the gantry may be arranged and/or configured in other ways, e.g., for linear and/or translative relative movement. For example, the X-ray source and detector may be moved together as an aggregate assembly unit along the table axis, commonly referred to as the z-axis, without rotation. Alternatively, the patient table is moved. In other words, an array of one or more source-detector combinations may scan along a horizontally arranged table top, or even vertically along a standing object.

For a better understanding, the proposed technology will now be described in further detail with reference to FIGS. 10-14 illustrating non-limiting examples of the data processing and data transfer according to the invention. These particular examples are illustrated with reference to a CT architecture, but are not limited thereto, as just explained.

Figure 10:
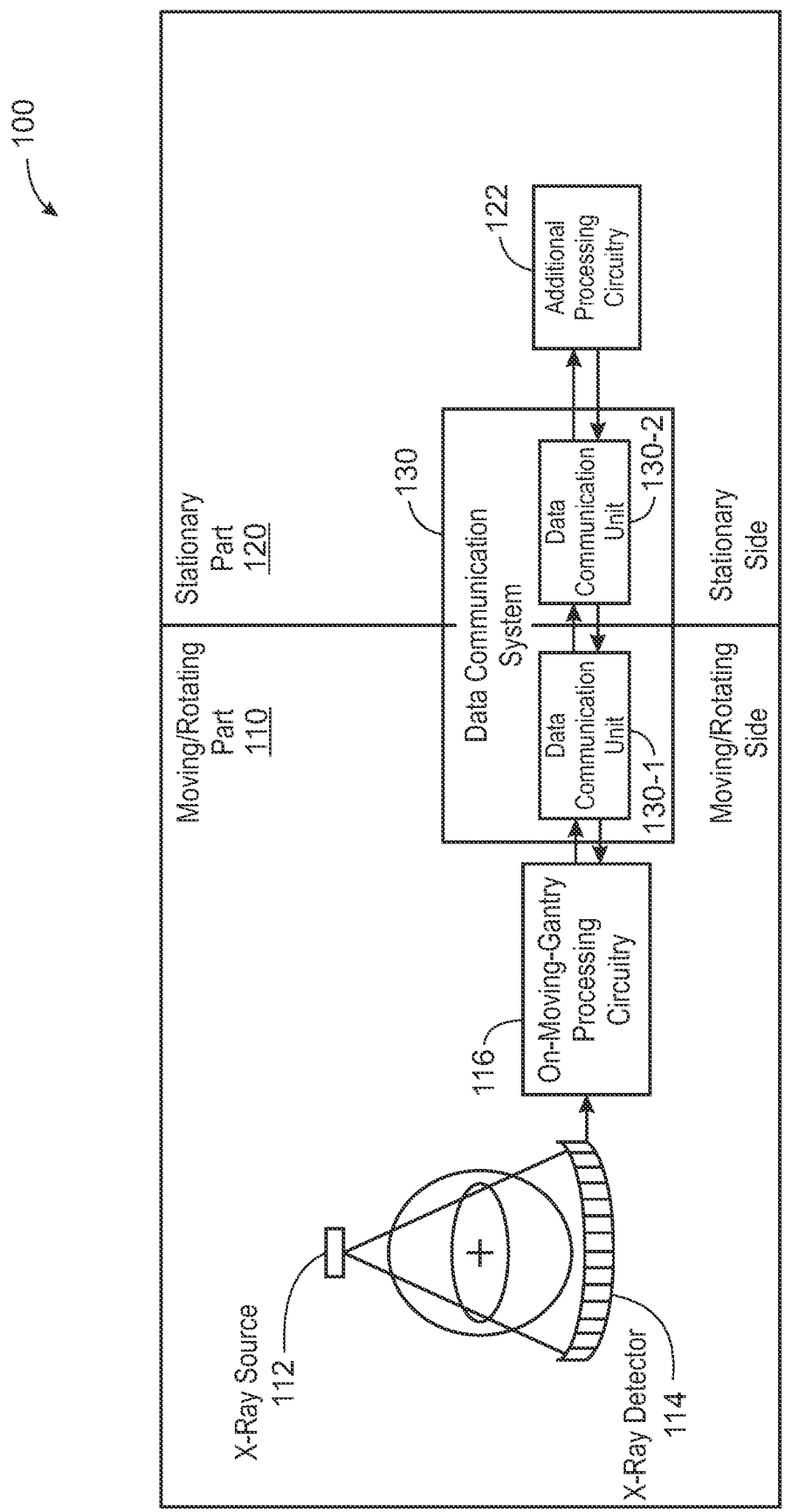
FIG. 10 schematically shows a CT imaging system according to an exemplifying embodiment.

FIG. 10 schematically shows a CT imaging system according to an exemplifying embodiment. The overall CT system 100 comprises a gantry with a moving/rotating part 110 on a moving/rotating side and a stationary part 120 on a stationary side. The moving/rotating part 110 includes an X-ray source 112 and an X-ray detector 114, as well as processing circuitry 116, referred to as on-moving-gantry processing circuitry.

The moving/rotating part 110 and the stationary part 120 are communicatively coupled via a data communication system 130. In this example, the data communication system 130 comprises a first data communication unit 130-1 on the moving/rotating part on the moving/rotating side and a second data communication unit 130-2 on the stationary part on the stationary side.

The on-moving-gantry processing circuitry 116 is configured to determine, for each of a number of partial data sets of the generated detector data, a metric value of at least one metric, the metric value being translatable into a type of data management for the partial data set among at least two different types of data management.

The on-moving-gantry processing circuitry 116 is further configured to decide, for each partial data set, how the partial data set is to be treated in dependence on the determined metric value of said at least one metric and to selectively effectuate data management according to the corresponding type of data management.

By way of example, the on-moving-gantry processing circuitry 116 may be configured to identify at least two different partial data sets of the generated detector data for which different types of data management are to be applied.

For example, the different types of data management may include i) performing on-moving-gantry data processing, such as data reduction, of the partial data set of the generated detector data before transmission of the partial data set from the moving part to the stationary part, ii) performing no on-moving-gantry data processing of the partial data set of the generated detector data before transmission of the partial data set from the moving part to the stationary part, and/or iii) omitting transmission of the partial data set of the generated detector data.

Optionally, the stationary part 120 comprises additional processing circuitry 122 for performing various processing operations such as filtering operations, calibration, pile-up correction, material decomposition and/or image reconstruction.

Figure 11:
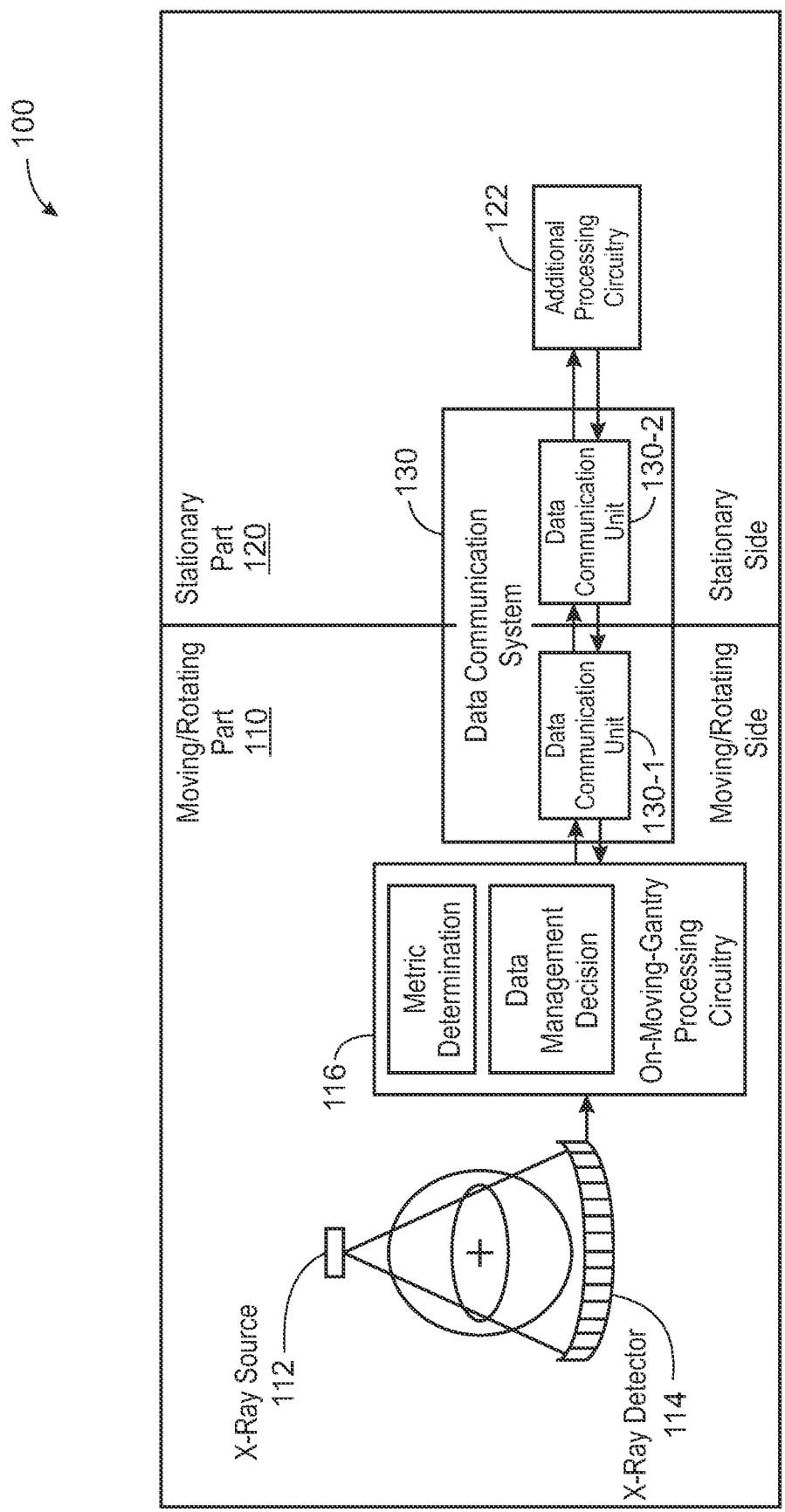
FIG. 11 schematically shows a CT imaging system according to another exemplifying embodiment.

FIG. 11 schematically shows a CT imaging system according to another exemplifying embodiment. FIG. 11 is similar to FIG. 10, but illustrated with a metric determination module and a data management decision module in the on-moving-gantry processing circuitry 116. For example, these modules may be implemented as software modules for performing the functions and/or operations as described herein. Alternatively, the modules may be implemented as specialized hardware circuits, e.g., FPGA or ASIC, definable as part of the overall on-moving-gantry processing circuitry 116.

Figure 12:
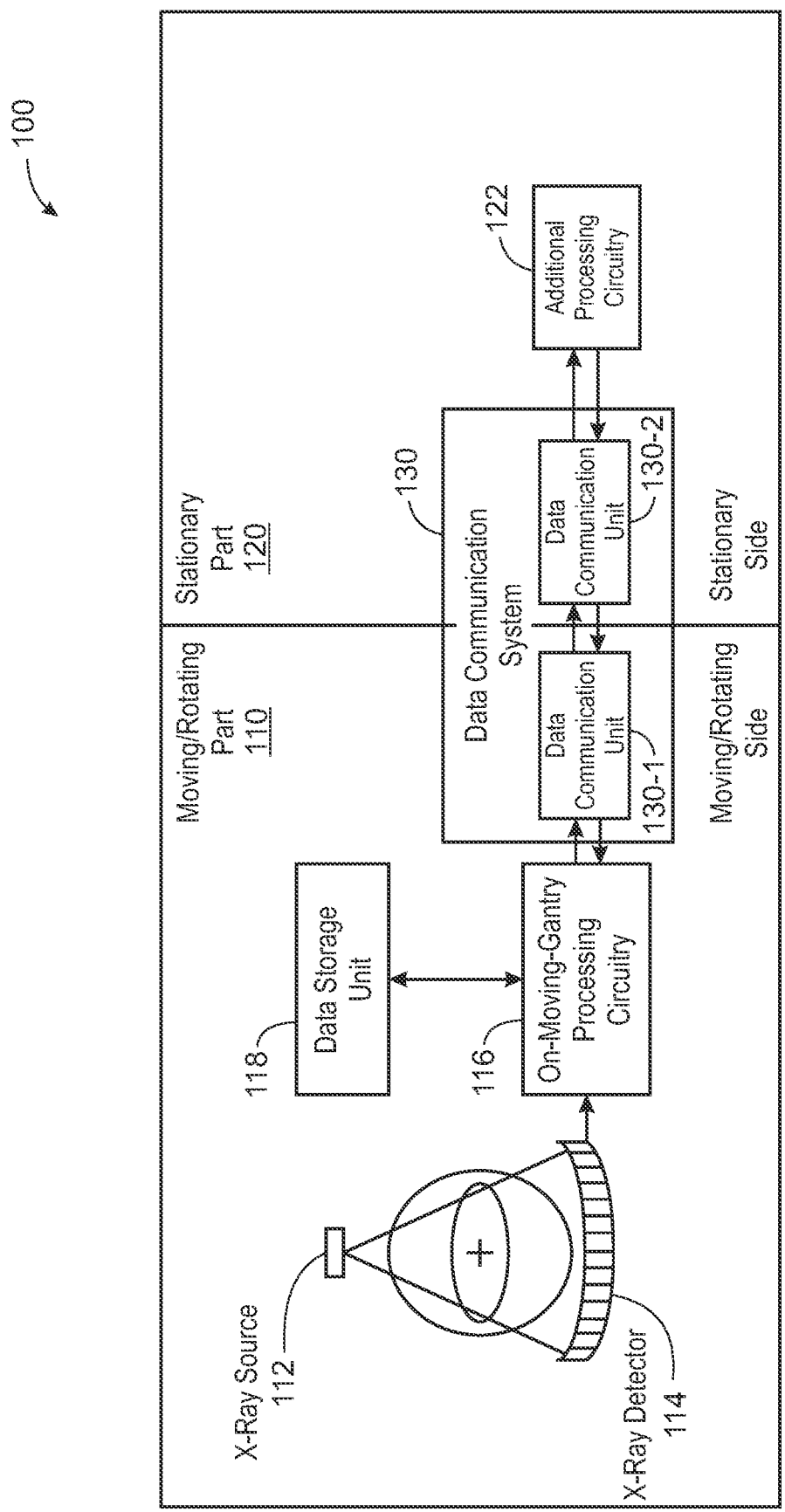
FIG. 12 schematically shows a CT imaging system according to yet another exemplifying embodiment.

FIG. 12 schematically shows a CT imaging system according to yet another exemplifying embodiment. FIG. 12 is also similar to FIG. 10, except for an additional data storage unit 118 provided on the moving/rotating part 110. The data storage unit 118 is connectable to the on-moving-gantry processing circuitry 116 for use during data processing operations.

For example, the data storage unit 118 may comprise a dedicated large memory, for example, non-volatile memory express (NVMe). The data storage unit 118 may comprise, in addition or alternatively, a temporary memory needed during continuous data processing, for example, ASIC, field-programmable gate array (FPGA) register or memory. The data storage unit 118 may comprise, in addition or alternatively, a RAM (random access memory). It should also be understood that there may be a set of transitory registers that is normally defined as part of the processing circuitry 116, when configured as a normal processor.

Figure 13:
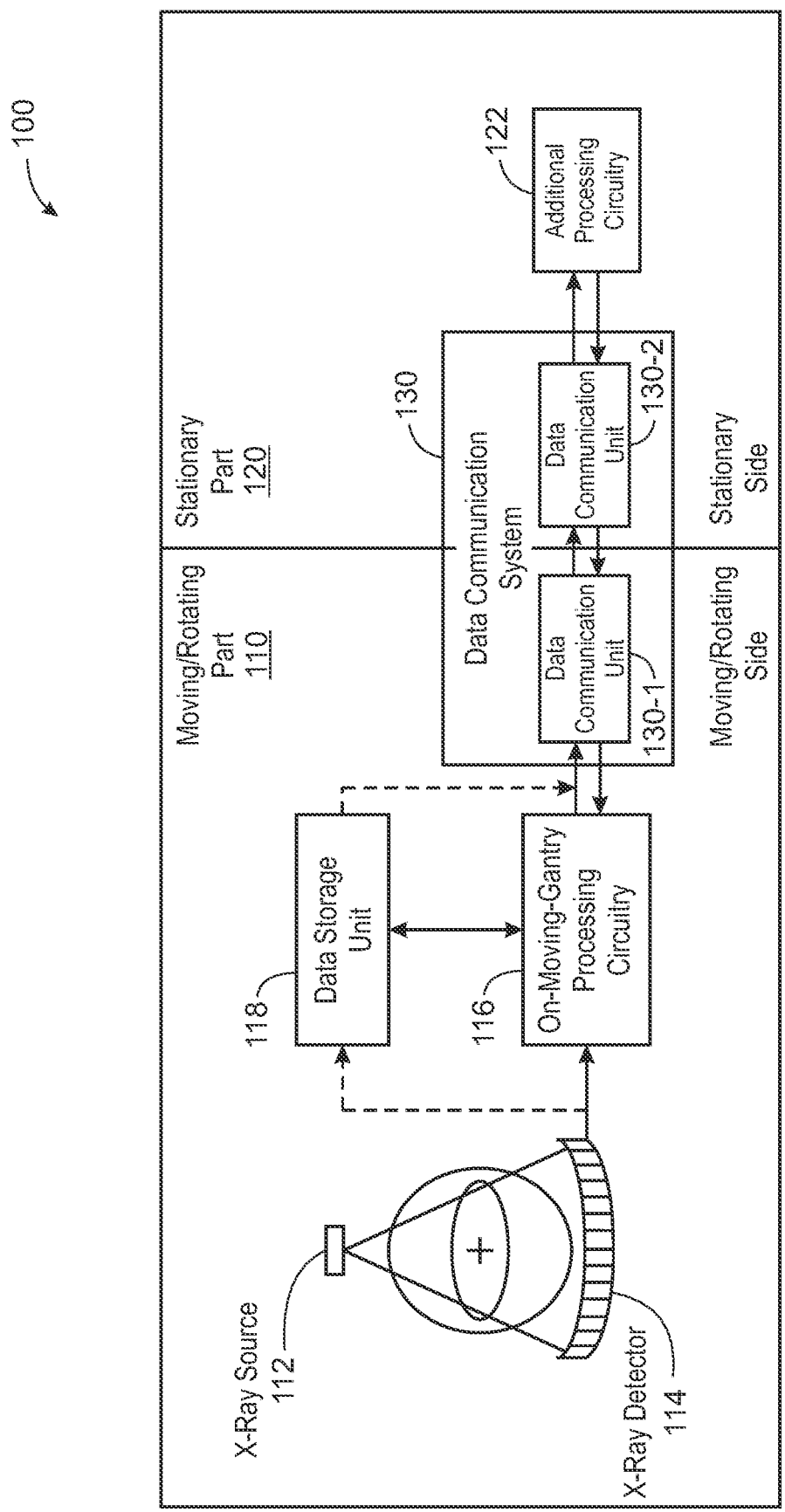
FIG. 13 schematically shows a CT imaging system according to still another exemplifying embodiment.

FIG. 13 schematically shows a CT imaging system according to still another exemplifying embodiment. FIG. 13 is similar to FIG. 12, with the addition of an optional data path more or less directly from the X-ray detector 114 to the data storage unit 118, and an optional data path from the data storage unit 118 to the data communication system 130. This means that detector data from the X-ray detector 114 may, if desirable, be transferred directly to the data storage unit 118. The processing circuitry 116 and the data storage unit 118 may then interact for exchange of data to be processed and/or analyzed. This also means that processed and/or unprocessed data stored in the data storage unit 118 may be transferred more or less directly to the data communication unit 130-1 on the moving/rotating part 110 for transfer to the data communication unit 130-2 on the stationary part 120.

Figure 14:
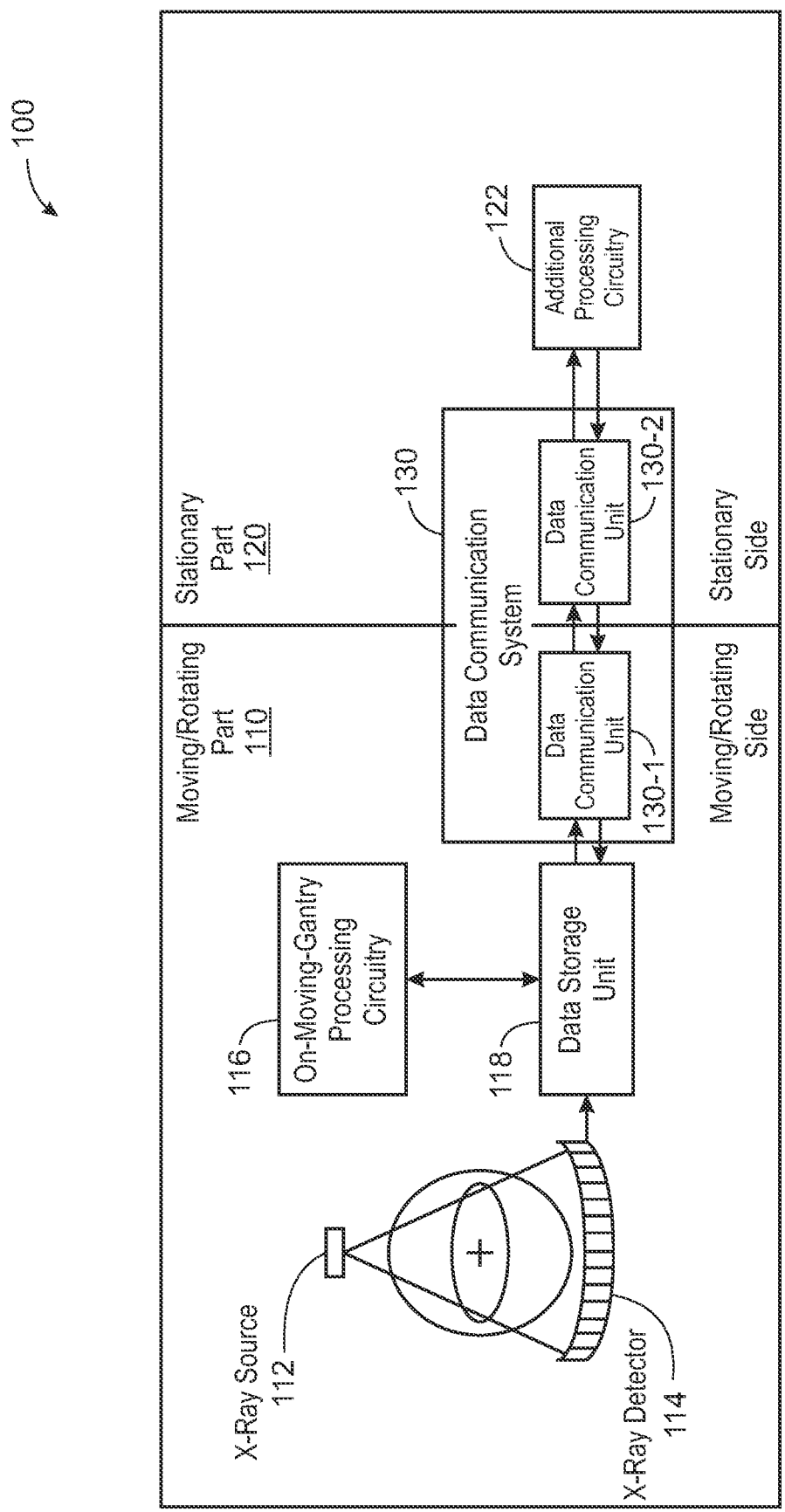
FIG. 14 schematically shows a CT imaging system according to yet another exemplifying embodiment.

FIG. 14 schematically shows a CT imaging system according to yet another exemplifying embodiment. In this particular example, the data storage unit 118 is connected more or less directly to the X-ray detector 114 to receive and at least temporarily store the detector data. The data storage unit 118 and the processing circuitry 116 are interconnected to enable exchange of detector data for processing and/or analysis by the processing circuitry 116 and/or exchange of processed data from the processing circuitry 116 back to the data storage unit 118. Data in processed and/or unprocessed form may then be selectively transferred, e.g., under the control of the processing circuitry 116, from the data storage unit 118 to the data communication unit 130-1 on the moving/rotating part 110 for transfer to the data communication unit 130-2 on the stationary part 120.

The proposed technology will now be described with reference to non-limiting examples related to pulse pileup processing. As should be clear by now, the proposed technology is not limited to this particular application, but generally applicable for metric-based differential data management.

As mentioned, pulse pileup occurs in photon-counting X-ray detectors when more than one photon hits the detector within the time window that is set by the pulse width in the electronics (the so-called dead time). Pileup may lead to a loss of counts because two or more photons end up generating just a single pulse. Pileup may also lead to spectral distortion because pulses within a dead time will add to a larger pulse height, which is interpreted as one photon with higher energy, and the pulses will also add to a wider pulse with a tail that may be detected as a second low-energy pulse, or in turn may pileup with subsequent pulses.

The effects of pileup on a radiological image include:
Reduced contrast-to-noise ratio because the increased loss of counts at higher count rates reduces the contrast between areas with different count rates, such as a radiological target.
Bias in a material-decomposed image because the spectral response of the detector varies with count rate and will be different from the calibrated spectral response if the X-ray tube current is different than at calibration.
Reduced efficiency of standard X-ray imaging correction processes, such as scatter correction, and data reduction operations, such as binning of pixels or depth segments, because these processes and operations typically assume a linear detector response.

In modalities such as photon counting computed tomography (PCCT), pulse pileup leads to lack of linearity in detector response as a function of the incident radiation flux. However, by means of, for example, bowtie filters, as well as judicious protocol design and patient positioning, high levels of pileup may be avoided for the vast majority of detector pixels. However, the large level of pileup for rays that pass through lesser material thicknesses may render the corresponding detector pixels more difficult to correct for pileup. Also, for off-center anatomies, the bowtie filter will perform less well in terms of minimizing pileup.

A major advantage offered by photon counting imaging technology is the ability to use smaller pixels and thus obtain higher resolution. Small pixels also help to reduce the pileup that occurs per pixel. Dividing each pixel into multiple depth segments helps decrease pileup further. However, with the vast number of pixels and/or the presence of multiple depth segments per pixel and/or multiple energy bins per pixel, the amount of data to be processed challenges the limits of state-of-the-art computing and data transmission technology. For example, if data processing of incoming events is performed on the moving/rotating part of the gantry, limited physical space, electric power, and cooling limit the computational resources available. If processing takes place outside the stationary part of the gantry, the gantry slip ring data transmission bandwidth becomes a limiting factor.

In a particular example embodiment, raw data may be analyzed on the moving/rotating part of the gantry to determine one or more metrics estimating the amount of pileup within each measurement (or group of measurements). This could also be estimated from a prior image, a preliminary image, pre-scan data, or a patient model.

Depending on the amount of pileup estimated, different processing may be applied, for example:
a. No correction or a correction incurring lower computational cost may be applied to data from detection elements that have no, or little pileup, respectively. Ideally, this correction is conducted on the rotating part of the gantry, and the output data are dimension-reduced by the pileup correction process. Dimension reduction, also referred to as data reduction, may be performed by methods such as detector segment summing, detector segment weighted-summing, principal components analysis, expression in terms of a dimension-reduced mathematical basis.
b. A more advanced (and perhaps computationally expensive) pileup correction may be reserved for pixels that score higher on the pileup metric(s) and are thus more difficult to correct. Because step (a) increases the available transmission bandwidth for these measurements, these measurements may be transmitted without compression, summing or expression in terms of another mathematical basis. The advanced pileup correction algorithm can then be performed off the rotating part of the gantry where more computational resources, space, power, and cooling are available.
c. Measurements corresponding to rays that travel exclusively through air may be identified using an appropriate metric estimated on the rotating part of the gantry and may be completely omitted from any transmission.
d. An identifier, containing one or more bits of information may identify transmitted data that represent whether measurements are to be treated as case (a) vs case (b). Similarly, if there are more than two types of treatment, more bits may be used to make the identification. For example, two bits of information could encode {high pileup, medium pileup, low pileup, no pileup}.

In photon counting systems, pileup correction is often followed by a material decomposition (MD) operation that expresses the data in terms of two of more material basis functions. Data from (a) may be applied to an MD algorithm configured to operate on data of a lower dimension than the MD algorithm that is configured to process data from (b). This may achieve substantial computational savings, while preserving MD fidelity for the challenging decomposition problems posed by the (b) data. By "configuring" we imply any of algorithm design, optimization, covariance matrix estimation, calibration and/or spatial aggregation of detector data.

For more information on pileup and pileup correction as such, reference can be made to the following sections:

The pileup response by photon-counting detectors can be principally divided into two categories: paralyzable and non-paralyzable behavior, e.g., as described in "Radiation Detection and Measurement" by Glenn F. Knoll, 3rd edition, John Wiley & Sons Inc, pp. 632-642.

Paralyzable detectors have a dead time that is reset for every new event, which results in an infinitely long dead time if the incident rate is high enough. Consequently, a maximum detected count rate is reached for some incident rate, after which the detected count rates starts to decrease. The detected count rate as a function of incident rate is hence not an injective and invertible function and it is challenging to correct for lost counts.

Non-paralyzable detectors, on the other hand, have a non-extendable (or semi-extendable) dead time, which results in a monotonically increasing (and generally invertible) detected count rate as a function of incident count rate. The detected count rate will reach a plateau at a maximum count rate determined by the reciprocal of the dead time.

For non-paralyzable photon-counting detectors without energy discrimination, well-established models are available that describe the loss of counts due to pileup with high accuracy, e.g., see "Radiation Detection and Measurement" by Glenn F. Knoll, 3rd edition, John Wiley & Sons Inc, pp. 632-642 and "Count statistics of non-paralyzable photon-counting detectors with nonzero pulse length", Grönberg F, Danielsson M, Sjölin M., Med Phys. 2018; 45(8):3800-3811. These models can be inverted and allow for correction of the lost counts.

For photon-counting detectors with energy discrimination, it is desirable to compensate also for spectral distortion, i.e., migration of counts between the energy bins. The correction problem then becomes even more complex, in particular because the bin response function is not, in general, an injective function of the true bin count rate even for non-paralyzable detectors. For low-energy bins, counts may be lost to higher energy bins faster than the increase in bin count rate, which results in a maximum count rate and a drop towards higher rates. This behavior makes it challenging to determine the inverse as there is no one-to-one mapping between detected and true count rate.

One approach for so-called spectral pileup correction is to model the pileup process analytically, e.g., see "First principles pulse pile-up balance equation and fast deterministic solution", Sabbatucci L, Fernández J E., Radiat Phys Chem. 2017; 137:12-17 and "Evaluation of models of spectral distortions in photon-counting detectors", Cammin J, Kappler S, Weidinger T, Taguchi K. J Med Imaging. 2016; 3(2). The model can be inverted, analytically or iteratively, to correct for the effects of pileup. One drawback of this approach is that more or less detailed system knowledge is required (incident spectrum, pulse shape etc.), which is not always available.

Another approach is to use data-driven methods based on neural networks or machine learning, e.g., see "Neural-networks-based Photon-Counting Data Correction: Pulse Pileup Effect", Feng R, Rundle D, Wang G, In: IEEE.; 2018:1-14 and "Near optimal neural network estimator for spectral X-ray photon counting data with pileup", Alvarez, ArXiv. 2017:1-11. This approach does not require any high level of system knowledge.

A more advanced and efficient procedure for pileup correction is proposed in U.S. Pat. No. 11,166,683, which discloses a method and corresponding system for pileup correction in a non-paralyzable energy-discriminating photon-counting X-ray detector operating based on a number of energy bins. The procedure involves adding, for each of a number of energy bins, a correction term to the detected signal of the energy bin, said correction term being a product of two separable parameterized functions, each of which includes at least one parameter, where a first parameterized function depends on a weighted sum of the detected signal over the energy bins, and where a second parameterized function depends on the detected signal(s) in one or several energy bin(s).

Figure 15:
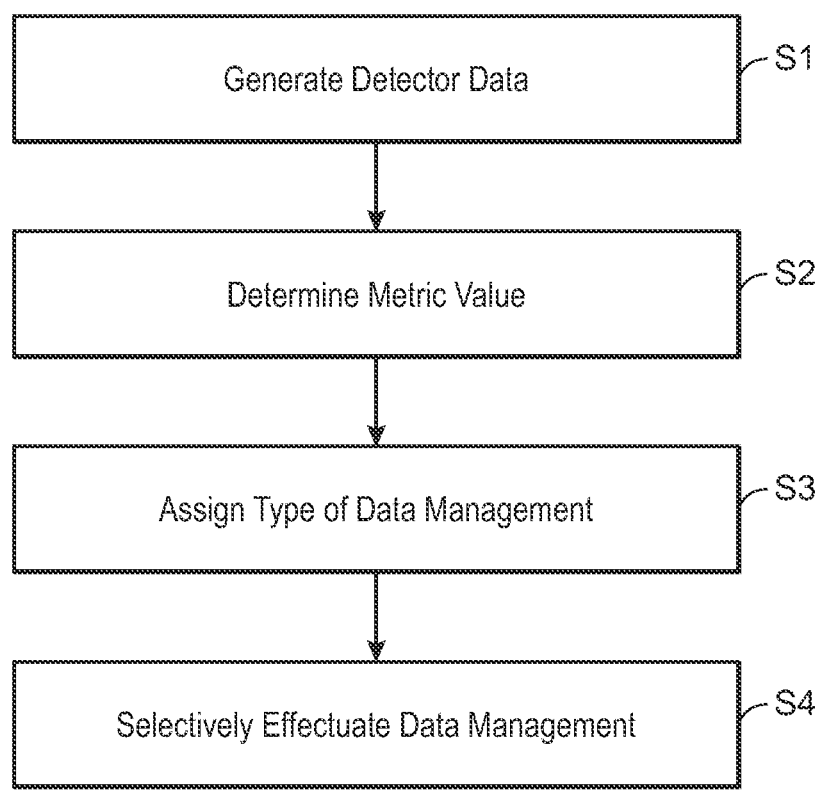
FIG. 15 is a schematic flow diagram illustrating an example of a method of operating a CT imaging system.

FIG. 15 is a schematic flow diagram illustrating an example of a method of operating a CT imaging system.

According to a second aspect there is provided a method of operating an X-ray imaging system. The X-ray imaging system has a gantry including a moving part on a moving side and a stationary part on a stationary side, the moving part and the stationary part being communicatively coupled via a data communication system. The moving part comprises an X-ray source configured to emit X-rays, an X-ray detector configured to generate detector data, and on-moving-gantry processing circuitry.

Basically, the method comprises the following steps:
S1: the X-ray detector generating detector data;
S2: the on-moving-gantry processing circuitry determining, for each of a number of partial data sets of the generated detector data, a metric value of at least one metric based on the detector data of the partial data set;
S3: the on-moving-gantry processing circuitry assigning a type of data management for the partial data set among at least two different types of data management in dependence on the determined metric value, and
S4: the on-moving-gantry processing circuitry selectively effectuating data management for the partial data set according to the assigned type of data management.

As mentioned, at least some of the steps, functions, procedures, and/or blocks described herein may be implemented in software such as a computer program for execution by suitable processing circuitry such as one or more processors or processing units.

According to a third aspect there is provided a computer-program product comprising a non-volatile computer-readable storage medium having stored thereon a computer program. The computer program comprises instructions, which when executed by processing circuitry arranged on a moving part of the gantry of an X-ray imaging system, cause the processing circuitry to:
determine, for each of a number of partial data sets of detector data generated by an X-ray detector of the X-ray imaging system, a metric value of at least one metric based on the detector data of the partial data set;
assign a type of data management for the partial data set among at least two different types of data management in dependence on the determined metric value,
selectively effectuate data management for the partial data set according to the assigned type of data management.

Figure 16:
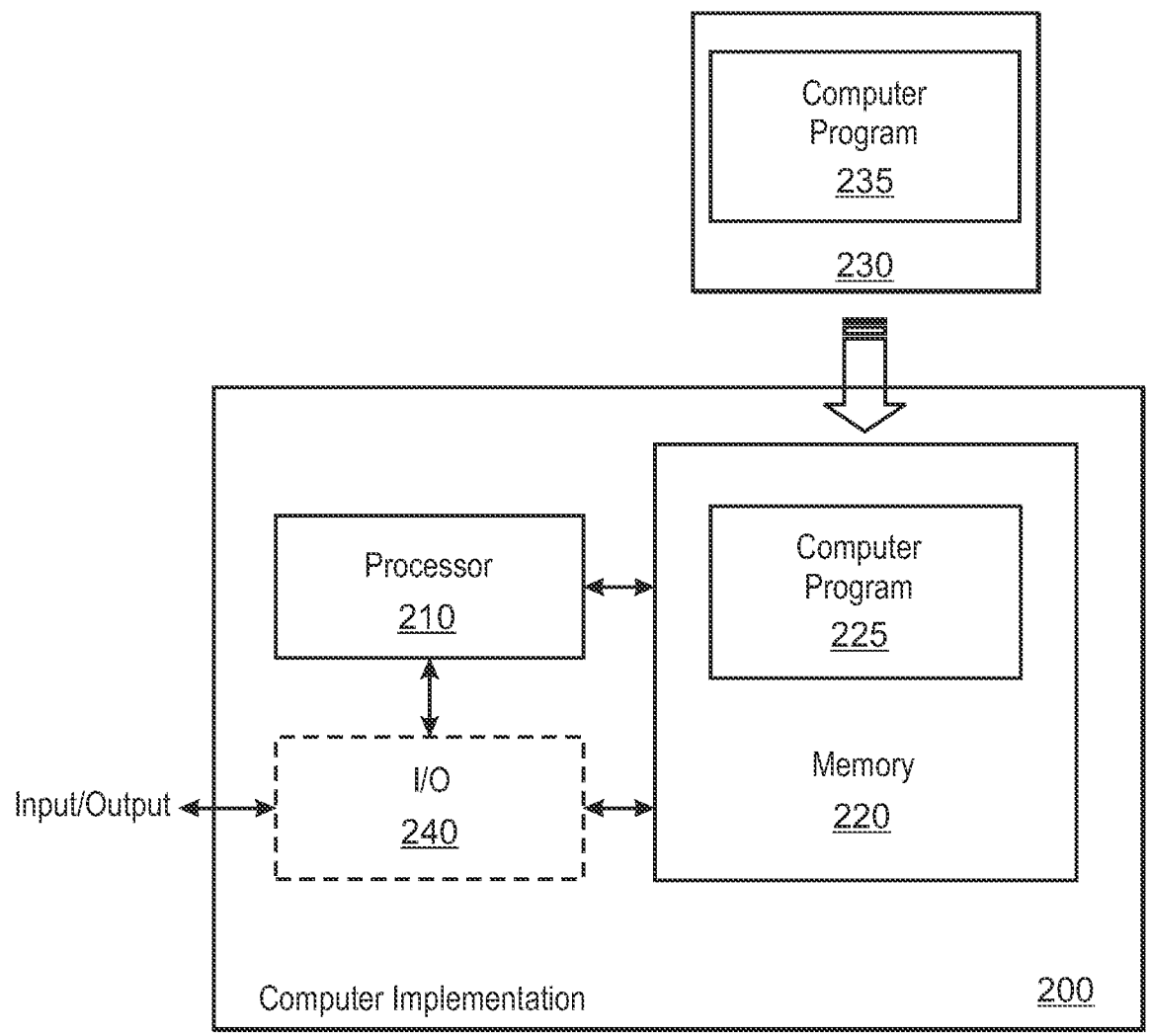
FIG. 16 is a schematic diagram illustrating an example of a computer implementation according to an embodiment.

FIG. 16 is a schematic diagram illustrating an example of a computer implementation according to an embodiment. In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

In a particular example, the memory 220 comprises a set of instructions executable by the processor, whereby the processor is operative to perform the steps and/or actions described herein.

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

Method flows may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively, it is possible to realize the modules predominantly by hardware modules, or alternatively by hardware. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the present scope as defined by the appended claims.

It is further noted that the inventive concepts relate to all possible combinations of features unless explicitly stated otherwise. In particular, different part solutions in the different embodiments can be combined in other configurations, where technically possible.

The invention claimed is:

1. An X-ray imaging system comprising:
a gantry including a moving part on a moving side and a stationary part on a stationary side, the moving part and the stationary part being communicatively coupled via a data communication system;
wherein the moving part comprises:
an X-ray source configured to emit X-rays;
an X-ray detector configured to generate detector data; and
on-moving-gantry processing circuitry,
wherein said on-moving-gantry processing circuitry is configured to determine, for each of a number of partial data sets of the generated detector data, a metric value of at least one metric, the metric value being translatable into a type of data management for the partial data set among at least two different types of data management;
wherein said on-moving-gantry processing circuitry is configured to decide, for each partial data set, how the partial data set is to be treated in dependence on the determined metric value of said at least one metric and to selectively effectuate data management according to the corresponding type of data management.

2. The X-ray imaging system of claim 1, wherein said X-ray imaging system is a Computed Tomography (CT) system, and said moving part and said stationary part are a rotating part and a stationary part of the gantry of the CT system.

3. The X-ray imaging system of claim 1, wherein said on-moving-gantry processing circuitry is configured to identify at least two different partial data sets of the generated detector data for which different types of data management are to be applied.

4. The X-ray imaging system of claim 1, wherein said at least two different types of data management include at least one of the following:
i) performing on-moving-gantry data processing of the partial data set of the generated detector data before transmission of the partial data set from the moving part to the stationary part,
ii) performing no on-moving-gantry data processing of the partial data set of the generated detector data before transmission of the partial data set from the moving part to the stationary part, and
iii) omitting transmission of the partial data set of the generated detector data.

5. The X-ray imaging system of claim 4, wherein said on-moving-gantry processing circuitry is further configured to perform on-moving-gantry data processing of different levels of computational complexity for different partial data sets.

6. The X-ray imaging system of claim 1, wherein said on-moving-gantry processing circuitry is configured to decide, based on the determined metric value of said at least one metric for a first partial data set, that on-moving-gantry data processing of the first partial data set is to be applied before transmission from the moving part to the stationary part, and
wherein said on-moving-gantry processing circuitry is configured to decide, based on the determined metric value of said at least one metric for a second partial data set, that the second partial data set is to be transmitted from the moving part to the stationary part without on-moving-gantry data processing, or that on-moving-gantry data processing of a lower level of computational complexity than for said first partial data set is to be applied to the second partial data set before transmission from the moving part to the stationary part.

7. The X-ray imaging system of claim 6, wherein said on-moving-gantry processing circuitry is configured to perform on-moving-gantry data processing of the first partial data set by data reduction to generate a reduced first partial data set for transmission from the moving part to the stationary part.

8. The X-ray imaging system of claim 7, wherein said X-ray imaging system further comprises additional processing circuitry in connection with the stationary part, said additional processing circuitry being configured to perform a material decomposition procedure adapted for the reduced first partial data set.

9. The X-ray imaging system of claim 1, wherein said on-moving-gantry processing circuitry is configured to decide, based on the determined metric value of said at least one metric for a specific partial data set, that said specific partial data set is to be omitted from transmission from the moving part to the stationary part.

10. The X-ray imaging system of claim 1, wherein said on-moving-gantry processing circuitry is configured to determine in which one of at least two non-overlapping intervals the determined metric value of said at least one metric resides, each interval being associated with a respective one of said at least two different types of data management, to thereby enable associating the determined metric value with a specific type of data management for the considered partial data set.

11. The X-ray imaging system of claim 1, wherein said at least one metric includes a pileup metric representing an amount of pulse pileup within at least part of the considered partial data set of the generated detector data, and
wherein said on-moving-gantry processing circuitry is configured to decide, in dependence on the determined metric value of said pileup metric, whether on-moving-gantry pileup correction data processing is to be applied to the partial data set and to selectively effectuate said on-moving-gantry pileup correction data processing of the partial data set to generate a corrected data set.

12. The X-ray imaging system of claim 11, wherein additional off-moving-gantry pileup correction data processing of the corrected data set is performed by processing circuitry on the stationary part.

13. The X-ray imaging system of claim 11, wherein said on-moving-gantry processing circuitry is configured to perform on-moving-gantry pileup correction data processing when the determined metric value of said pileup metric indicates an amount of pileup that is higher than zero but lower than a first threshold level.

14. The X-ray imaging system of claim 11, wherein said on-moving-gantry processing circuitry is configured to decide that the partial data set is to be transmitted from the moving part to the stationary part without on-moving-gantry pileup correction data processing when the determined metric value of said pileup metric indicates an amount of pileup that is higher than a second threshold level.

15. The X-ray imaging system of claim 14, wherein off-moving-gantry pileup correction data processing of the partial data set is performed by processing circuitry on the stationary part.

16. The X-ray imaging system of claim 11, wherein said on-moving-gantry processing circuitry is configured to determine said pileup metric based on a comparison between estimated true photon counts and measured photon counts.

17. The X-ray imaging system of claim 1, wherein said at least one metric includes an X-ray propagation metric or X-ray attenuation metric.

18. The X-ray imaging system of claim 17, wherein said on-moving-gantry processing circuitry is configured to identify a partial data set in which the detector data corresponds to X-rays travelling exclusively through air from the X-ray source the X-ray detector based on said X-ray propagation metric or X-ray attenuation metric, and wherein said on-moving-gantry processing circuitry is configured to decide that the identified partial data set is to be omitted from transmission from the moving part to the stationary part.

19. The X-ray imaging system of claim 1, wherein each partial data set corresponds to a batch of the generated detector data that is related to an X-ray measurement or a group of X-ray measurements.

20. The X-ray imaging system of claim 1, wherein said data communication system is configured to transmit, for at least one partial data set, a representation of the corresponding determined metric value, or an identifier representing the type of applied data management, from the moving part to the stationary part in association with the partial data set.

21. The X-ray imaging system of claim 20, wherein said identifier indicates whether on-moving-gantry data processing of the partial data set has been performed.

22. The X-ray imaging system of claim 1, wherein the data communication system comprises a first data communication unit on the moving part on the moving side and a second data communication unit on the stationary part on the stationary side.

23. The X-ray imaging system according to claim 1, wherein the moving part comprises an on-moving-gantry data storage unit in connection with said on-moving-gantry processing circuitry for storage of the detector data in processed and/or unprocessed form.

24. The X-ray imaging system of claim 1, wherein the X-ray detector is a photon-counting detector.

25. A method of operating an X-ray imaging system having a gantry including a moving part on a moving side and a stationary part on a stationary side, the moving part and the stationary part being communicatively coupled via a data communication system, wherein the moving part comprises an X-ray source configured to emit X-rays, an X-ray detector configured to generate detector data, and on-moving-gantry processing circuitry, said method comprising:
said X-ray detector generating detector data;
said on-moving-gantry processing circuitry determining, for each of a number of partial data sets of the generated detector data, a metric value of at least one metric based on the detector data of the partial data set;
said on-moving-gantry processing circuitry assigning a type of data management for the partial data set among at least two different types of data management in dependence on the determined metric value, and
said on-moving-gantry processing circuitry selectively effectuating data management for the partial data set according to the assigned type of data management.

26. A non-transitory computer-program product comprising a non-volatile computer-readable storage medium having stored thereon a computer program, said computer program comprising instructions, which when executed by processing circuitry arranged on a moving part of an X-ray imaging system, cause said processing circuitry to: —determine, for each of a number of partial data sets of detector data generated by an X-ray detector of the X-ray imaging system, a metric value of at least one metric based on the detector data of the partial data set; —assign a type of data management for the partial data set among at least two different types of data management in dependence on the determined metric value, —selectively effectuate data management for the partial data set according to the assigned type of data management.

* * * * *